(12) United States Patent
Desai et al.

(10) Patent No.: US 7,220,753 B2
(45) Date of Patent: *May 22, 2007

(54) 2,7-SUBSTITUTED OCTAHYDRO-1H-PYRIDO[1,2-A]PYRAZINE DERIVATIVES AS LIGANDS FOR SEROTONIN RECEPTORS

(75) Inventors: Kishor A. Desai, Ledyard, CT (US); Anton F. Fliri, Stonington, CT (US); Mark A. Sanner, Old Saybrook, CT (US)

(73) Assignee: Pfizer Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/852,611

(22) Filed: May 24, 2004

(65) Prior Publication Data

US 2004/0214830 A1  Oct. 28, 2004

Related U.S. Application Data

(63) Continuation of application No. 10/213,604, filed on Aug. 7, 2002, now abandoned, which is a continuation of application No. 09/784,567, filed on Feb. 15, 2001, now abandoned, which is a continuation of application No. 09/368,984, filed on Aug. 5, 1999, now Pat. No. 6,231,833, which is a continuation-in-part of application No. 09/135,946, filed on Aug. 18, 1998, now abandoned, which is a continuation-in-part of application No. 08/809,145, filed on Mar. 26, 1997, application No. PCT/IB95/00689, filed on Aug. 24, 1995, now Pat. No. 5,852,031, which is a continuation of application No. 08/315,470, filed on Sep. 30, 1994, now abandoned.

(51) Int. Cl.
   - *A01N 43/42* (2006.01)
   - *A61K 31/44* (2006.01)

(52) U.S. Cl. ............... 514/279; 544/358; 544/359; 544/336; 424/1.65; 424/1.11

(58) Field of Classification Search ............... 424/1.11, 424/1.37, 1.65, 9.1, 9.2; 514/249, 279; 544/224, 544/295, 336, 358, 359

See application file for complete search history.

(56) References Cited

U.S. PATENT DOCUMENTS

| | | | |
|---|---|---|---|
| 5,122,525 A | 6/1992 | Bright et al. | |
| 5,602,128 A | 2/1997 | Baudy et al. | |
| 5,741,789 A | 4/1998 | Hibschman et al. | |
| 5,852,031 A * | 12/1998 | Desai et al. | 514/279 |
| 6,231,833 B1 * | 5/2001 | Desai et al. | 424/9.1 |

FOREIGN PATENT DOCUMENTS

| | | |
|---|---|---|
| EP | 512755 A2 | 11/1992 |
| EP | 759299 A1 | 2/1997 |
| HU | 216637 | 6/1998 |
| WO | WO 90/08144 | 7/1990 |
| WO | WO 90/08148 | 7/1990 |
| WO | WO 92/00074 | 1/1992 |
| WO | WO 96/23789 | 8/1996 |
| WO | WO 97/03068 | 1/1997 |
| WO | WO 97/08159 | 3/1997 |
| WO | WO 97/17343 | 5/1997 |
| WO | WO 99/52901 | 10/1999 |
| WO | WO 99/52907 | 10/1999 |

OTHER PUBLICATIONS

Reitz, Allen, et al., Orally Active Benzamidse Antipsychotic Agents with Affinity for Dopamine $D_2$, Serotonin $5\text{-}HT_{1A}$, and Adrenergic $\alpha_1$ Receptors, *Journal of Medicinal Chemistry*, 41(12): 1997-2009, 1998.

Taverne, Thierry, et al. "Novel Benzothiazolin-2-one and Benzoxazin-3-one Arylpiperazine Derivatives with Mixed $5HT_{1A}$/$D_2$ Affinity as Potential Atypical Antipsychotics", *J. Med. Chem.*, 41: 2010-2018 (1998).

De Vry, Jean, et al. "Characterization of the Aminomethylchrma Derviative BAY X 3702 as a Highly Potent 5-Hydroxytryptamine$_{1A}$ Receptor Antagonist", *J. Pharm. and Experim. Therap.*, 284(3): 1082-1094 (1998).

Sanner, Mark A., "Selective dopamine $D_4$ receptor antagonists" *Exp. Opin. Ther. Patents* 1998, 8(4), pp. 383-393.

Robertson, D.W. "Recent progress in serotonin (5-HT)1A receptor modulators", *Ann. Rep. Med. Chem.*, 1995 30, pp. 1-9.

Wolff, M.C. et al., "Pharmacological profile of LY301317, a potent and selective 5-HT1a agonist", *Drug Dev. Res.* 1997, 40, pp. 17-34.

MKC-242, *Drugs of the Future*, 1997, 22, pp. 225-228.

Sharma, R. P. Shapiro, L.E., "The 5HT1a receptor system: possible implication for schizophrenic negative symptomatology" *Psych. Ann.* 1996, 26 pp. 88-92.

(Continued)

*Primary Examiner*—Dameron L. Jones
(74) *Attorney, Agent, or Firm*—Mark J. Cohen; Charles W. Ashbrook; Rosanne Goodman

(57) ABSTRACT

Substituted pyrido[1,2-a]pyrazines of general formula I; wherein Ar and $Ar^1$ represent various carbocyclic and heterocyclic aromatic rings; A represents O, S, SO, $SO_2$, CHOH, C=O, or —$(CR^3R^4)$; and n is 0–2, as well as precursors thereto, are ligands for dopamine receptor subtypes and serotonin (5HT) within the body and are therefore useful in the treatment of disorders of the dopamine and serotonin systems:

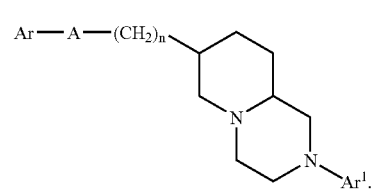

19 Claims, No Drawings

OTHER PUBLICATIONS

Wadenberg, M.L. "Serotonergic mechanisms in neuroleptic-induced catalepsy in the rat", *Neurosci. Biobehav. Rev.*, 1996, 20 pp. 325-339.

Artigas, R. et al., "Acceleration of the effect of selected antidepressant drugs in major depression by 5-HT1a antagonists", *Trends Neurosci.*, 1996, 19, pp. 378-383.

Shiue, C. Y. et al., "p-[18F]-MPPF: a potential radioligand for PET studies of 5-HT1a receptors in humans", *Synapse*, 1997, 25, pp. 147-154.

Ramage, A.G. and Fozard, John R., "Exidence that the putative 5-HT1a receptor agonists, 8-OH-DPAT and ipsapirone, have a central hypotensive action that differs from that of clonidine in anesthetized cats", *Eur. J. Pharmacol.*, 1987, 138, pp. 179-191.

DeVry, J., "5HT1a receptor agonists: recent developments and controversial issues", *Psychopharmacol.*, 1995, 12, 121, pp. 1-26.

McCall, R.B., Clement, M.E. "Role of serotonin 1A and serotonin 2 receptors in the central regulation of the cardiovascular system", *Pharmacol. Rev.*, 1994, 46, pp. 231-243.

Neal-Beliveau, et al., "Serotonergic involvement in haloperidol induced catalepsy", *J. Pharmacol. Exp. Ther.*, 1993, 265,pp. 207-217.

Izquierdo, et al. "Memory Formation: The Sequence of Biochemical Events in the Hippocampus and Its Connection to Activity in Other Brain Structures", *Neurobiology*, 68:285-316 (1997).

* cited by examiner

2,7-SUBSTITUTED OCTAHYDRO-1H-PYRIDO[1,2-A]PYRAZINE DERIVATIVES AS LIGANDS FOR SEROTONIN RECEPTORS

This application is a continuation of application U.S. Ser. No. 10/213,604 filed on Aug. 7, 2002 now abandoned which is a continuation under 35 U.S.C. § 120 of U.S. application Ser. No. 09/784,567 filed Feb. 15, 2001 now abandoned, which is a continuation of U.S. application Ser. No. 09/368,984 filed Aug. 5, 1999, now U.S. pat. No. 6,231,833, which is a continuation-in-part of U.S. application Ser. No. 09/135,946, filed Aug. 18, 1998, now abandoned, which was a continuation-in-part of 08/809,145, filed Mar. 26, 1997, the national stage of International Application PCT/IB95/00689 filed Aug. 24, 1995, now U.S. Pat. No. 5,852,031, issued Dec. 22, 1998. PCT/IB95/00689 was a continuation of U.S. application Ser. No. 08/315,470 filed Sep. 30, 1994, now abandoned.

Compounds of this invention have affinity for serotonin (5HT) receptors, especially the serotonin 1a receptor ($5HT_{1A}$), and are therefore useful for treatment of diseases or conditions which are caused by disorders of the serotonin system.

BACKGROUND OF THE INVENTION

The present invention relates to the use of pharmacologically active 2,7-substituted octahydro-1H-pyrido[1,2-a]pyrazine derivatives, and their acid addition salts. The compounds of this invention are ligands for serotonin receptor subtypes, especially the $5HT_{1A}$ receptor, and are therefore useful in the treatment of disorders that can be treated by altering (i.e., increasing or decreasing), serotonin mediated neurotransmission.

The pharmacologically active 2,7-substituted octahydro-1H-pyrido[1,2-a]pyrazine derivatives of the formula I, as defined below, are also ligands for dopamine receptor subtypes, especially the dopamine D4 receptor. They are useful in treating conditions or disorders, schizophrenia for example, that can be treated by altering (i.e., increasing or decreasing) dopamine mediated neurotransmission. The dopamine receptor binding activity of these compounds is described in more detail in U.S. Ser. No. 08/809,145, supra, now U.S. Pat. No. 5,852,031. This application (Ser. No. 08/809,145) is incorporated herein by reference in its entirety.

Serotonin plays a role in several psychiatric disorders, including anxiety, Alzheimer's disease, depression, nausea and vomiting, eating disorders, and migraine. (See Rasmussen et al., "Chapter 1. Recent Progress in Serotonin (5HT)$_{1A}$ Receptor Modulators", in *Annual Reports in Medicinal Chemistry, Section I*, 30, pp. 1–9, 1995, Academic Press, Inc.; Antigas et al., *Trends Neurosci.*, 19 (9), 1996, pp. 378–383; and Wolf et al., *Drug Development Research*, 40, 1997, pp. 17–34.) Serotonin also plays a role in both the positive and negative symptoms of schizophrenia. (See Sharma et al., *Psychiatric Annals.*, 26 (2), February, 1996, pp. 88–92.)

SUMMARY OF THE INVENTION

This invention relates to a method of treatment of diseases or conditions which are caused by disorders of the serotonin system which comprises administering to a mammal in need of such treatment a compound of the formula

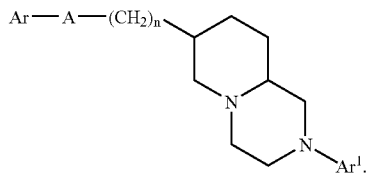

wherein Ar is phenyl, naphthyl, benzoxazolonyl, indolyl, indolonyl, benzimidazolyl, quinolyl, furyl, benzofuryl, thienyl, benzothienyl, oxazolyl, benzoxazolyl;

$Ar^1$ is phenyl, pyridinyl, pyridazinyl, pyrimidinyl, pyrazinyl;

A is O, S, SO, $SO_2$, C=O, CHOH, or —$(CR^3R^4)$—;

n is 0, 1 or 2;

each of Ar and $Ar^1$ may be independently and optionally substituted with one to four substituents independently selected from the group consisting of fluoro, chloro, bromo, iodo, cyano, nitro, thiocyano, —SR, —SOR, —$SO_2R$, —$NHSO_2R$, —$(C_1–C_6)$alkoxy, —$NR^1R^2$, —$NRCOR^1$, —$CONR^1R^2$, Ph, —COR, COOR, —$(C_1–C_6)$alkyl, trifluoromethoxy, and —$(C_1–C_6)$alkyl substituted with one to six halogens, —$(C_3–C_6)$cycloalkyl, or trifluoromethoxy;

each and every R, $R^1$, and $R^2$ is independently selected from the group consisting of hydrogen, —$(C_1–C_6)$alkyl, —$(C_1–C_6)$alkyl substituted with one to thirteen halogens selected from fluorine, chlorine, bromine and iodine, phenyl, benzyl, —$(C_2–C_6)$alkenyl, —$(C_3–C_6)$cycloalkyl, and —$(C_1–C_6)$alkoxy;

each and every $R^3$ and $R^4$ is independently selected from a group consisting of hydrogen, methyl, ethyl, n-propyl, and i-propyl;

diastereomeric and optical isomers thereof; and pharmaceutically acceptable salts thereof.

This invention also provides a method of treatment of a disease or condition which is caused by a disorder of the serotonin system or a disorder of the dopamine system which comprises administering to a mammal in need of such treatment a compound of the formula

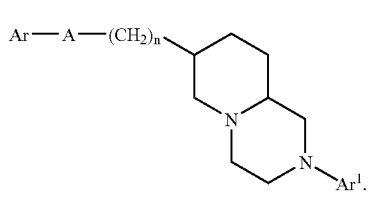

wherein Ar is phenyl, naphthyl, benzoxazolonyl, indolyl, indolonyl, benzimidazolyl, quinolyl, furyl, benzofuryl, thienyl, benzothienyl, oxazolyl, benzoxazolyl;

$Ar^1$ is phenyl, pyridinyl, pyridazinyl, pyrimidinyl, pyrazinyl;

A is O, S, SO, $SO_2$, C=O, CHOH, or —$(CR^3R^4)$—;

n is 0, 1 or 2;

each of Ar and $Ar^1$ may be independently and optionally substituted with one to four substituents independently selected from the group consisting of fluoro, chloro, bromo, iodo, cyano, nitro, thiocyano, —SR, —SOR, —$SO_2R$, —$NHSO_2R$, —$(C_1–C_6)$alkoxy, —$NR^1R^2$, —$NRCOR^1$, —$CONR^1R^2$, Ph, —COR, COOR, —$(C_1–C_6)$alkyl, trifluoromethoxy, and —(C₁–C₆)alkyl substituted with one to six halogens, —(C₃–C₆)cycloalkyl, or trifluoromethoxy;

each and every R, R¹, and R² is independently selected from the group consisting of hydrogen, —(C₁–C₆)alkyl, —(C₁–C₆)alkyl substituted with one to thirteen halogens selected from fluorine, chlorine, bromine and iodine, phenyl, benzyl, —(C₂–C₆)alkenyl, —(C₃–C₆)cycloalkyl, and —(C₁–C₆)alkoxy;

each and every R³ and R⁴ is independently selected from a group consisting of hydrogen, methyl, ethyl, n-propyl, and i-propyl; or a diastereomeric or optical isomers thereof; or a pharmaceutically acceptable salt thereof; in an amount effective to treat said disease or condition.

This invention also provides a method of treating a disorder or condition selected from the group consisting of migraine, headache, cluster headache, anxiety, depression, dysthymia, major depressive disorder, panic disorder, obsessive-compulsive disorder, posttraumatic stress disorder, avoidant personality disorder, borderline personality disorder, phobia, a disorder of cognition, a memory disorder, a learning disorder (including age related memory disorder) a neurodegenerative disease (including Alzheimer's disease), anxiety and/or depression associated with senile dementia or Alzheimer's disease, cancer (including prostate cancer), cerebral infarct (including that caused by stroke, ischemia or traumatic head injury), a sexual disorder, dizziness, an eating disorder, pain, chemical dependency or addiction, peptic ulcer, and attention deficit hyperactivity disorder in a mammal, comprising administering to said mammal an amount of a compound of the formula

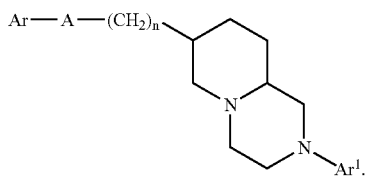

wherein Ar is phenyl, naphthyl, benzoxazolonyl, indolyl, indolonyl, benzimidazolyl, quinolyl, furyl, benzofuryl, thienyl, benzothienyl, oxazolyl, benzoxazolyl;

Ar¹ is phenyl, pyridinyl, pyridazinyl, pyrimidinyl, pyrazinyl;

A is O, S, SO, SO₂, C=O, CHOH, or —(CR³R⁴)—;

n is 0, 1 or 2;

each of Ar and Ar¹ may be independently and optionally substituted with one to four substituents independently selected from the group consisting of fluoro, chloro, bromo, iodo, cyano, nitro, thiocyano, —SR, —SOR, —SO₂R, —NHSO₂R, —(C₁–C₆)alkoxy, —NR¹R², —NRCOR¹, —CONR¹R², Ph, —COR, COOR, —(C₁–C₆)alkyl, trifluoromethoxy, and —(C₁–C₆)alkyl substituted with one to six halogens, —(C₃–C₆)cycloalkyl, or trifluoromethoxy;

each and every R, R¹, and R² is independently selected from the group consisting of hydrogen, —(C₁–C₆)alkyl, —(C₁–C₆)alkyl substituted with one to thirteen halogens selected from fluorine, chlorine, bromine and iodine, phenyl, benzyl, —(C₂–C₆)alkenyl, —(C₃–C₆)cycloalkyl, and —(C₁–C₆)alkoxy;

each and every R³ and R⁴ is independently selected from a group consisting of hydrogen, methyl, ethyl, n-propyl, and i-propyl; or a diastereomeric or optical isomers thereof; or a pharmaceutically acceptable salt thereof; effective to treat said disorder or condition.

In one embodiment of this method, the disorder or condition being treated is migraine, headache, or cluster headache.

In another embodiment, the disorder or condition being treated is anxiety, depression, dysthymia, major depressive disorder, panic disorder, obsessive-compulsive disorder, posttraumatic stress disorder, avoidant personality disorder, borderline personality disorder, or phobia.

In another embodiment, the disorder or condition being treated is a disorder of cognition, a memory disorder, a learning disorder (including age related memory disorder), or a neurodgenerative disease (including Alzheimer's disease). In another embodiment, the disorder is a learning disorder other than age related memory disorder. In a further embodiment, the disorder or condition is a neurodegenerative disease other than Alzheimer's disease. In still a further embodiment, the disorder or condition being treated is anxiety and/or depression associated with senile dementia or Alzheimer's disease.

In another embodiment of this method, the disorder or condition being treated is cancer. In one embodiment the cancer is prostate cancer; in another embodiment the cancer is a cancer other than prostate cancer.

In another embodiment, the disorder or condition being treated is cerebral infarct. The cerebral infarct can be a cerebral infarct caused by stroke, ischemia or traumatic head injury, or the cerebral infarct can have another cause.

In other embodiments of this method, the disorder or condition being treated is a sexual disorder, dizziness, an eating disorder, pain, chemical dependency or addiction, attention deficit hyperactivity disorder (ADHD), or peptic ulcer.

In another embodiment of this method, the condition is cerebral infarct and the compound of formula I is administered in combination with a 5HT₂ antagonist.

This invention also provides the above-recited methods, wherein the compound of formula I is administered in combination with a serotonin reuptake inhibitor.

This invention also provides a method of imaging an organ in a mammal, comprising administering to said mammal a radioactive form of a compound of the formula

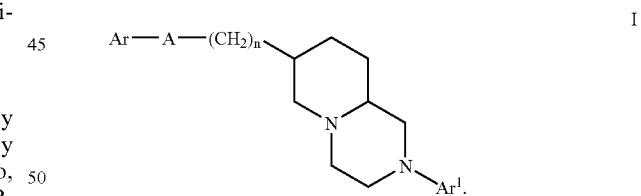

wherein Ar is phenyl, naphthyl, benzoxazolonyl, indolyl, indolonyl, benzimidazolyl, quinolyl, furyl, benzofuryl, thienyl, benzothienyl, oxazolyl, benzoxazolyl;

Ar¹ is phenyl, pyridinyl, pyridazinyl, pyrimidinyl, pyrazinyl;

A is O, S, SO, SO₂, C=O, CHOH, or —(CR³R⁴)—;

n is 0, 1 or 2;

each of Ar and Ar¹ may be independently and optionally substituted with one to four substituents independently selected from the group consisting of fluoro, chloro, bromo, iodo, cyano, nitro, thiocyano, —SR, —SOR, —SO₂R, —NHSO₂R, —(C₁–C₆)alkoxy, —NR¹R², —NRCOR¹, —CONR¹R², Ph, —COR, COOR, —(C₁–C₆)alkyl, trifluoromethoxy, and —(C₁–C₆)alkyl substituted with one to six halogens, —(C₃–C₆)cycloalkyl, or triflouromethoxy;

each and every R, R¹, and R² is independently selected from the group consisting of hydrogen, —(C₁–C₆)alkyl, —(C₁–C₆)alkyl substituted with one to thirteen halogens selected from fluorine, chlorine, bromine and iodine, phenyl, benzyl, —(C₂–C₆)alkenyl, —(C₃–C₆)cycloalkyl, and —(C₁–C₆)alkoxy;

each and every R³ and R⁴ is independently selected from a group consisting of hydrogen, methyl, ethyl, n-propyl, and i-propyl; or a diastereomeric or optical isomers thereof; or a pharmaceutically acceptable salt thereof;

and detecting the emissions of the radioactive compound.

This invention also provides a method of imaging an organ in a mammal, comprising administering to said mammal a compound of the formula

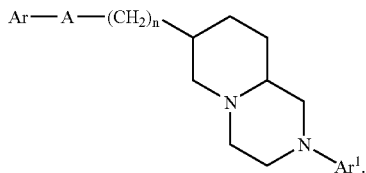

wherein Ar is phenyl, naphthyl, benzoxazolonyl, indolyl, indolonyl, benzimidazolyl, quinolyl, furyl, benzofuryl, thienyl, benzothienyl, oxazolyl, benzoxazolyl;

Ar¹ is phenyl, pyridinyl, pyridazinyl, pyrimidinyl, pyrazinyl;

A is O, S, SO, SO₂, C═O, CHOH, or —(CR³R⁴)—;

n is 0, 1 or 2;

each of Ar and Ar¹ may be independently and optionally substituted with one to four substituents independently selected from the group consisting of fluoro, chloro, bromo, iodo, cyano, nitro, thiocyano, —SR, —SOR, —SO₂R, —NHSO₂R, —(C₁–C₆)alkoxy, —NR¹R², —NRCOR¹, —CONR¹R², Ph, —COR, COOR, —(C₁–C₆)alkyl, trifluoromethoxy, and —(C₁–C₆)alkyl substituted with one to six halogens, —(C₃–C₆)cycloalkyl, or trifluoromethoxy;

each and every R, R¹, and R² is independently selected from the group consisting of hydrogen, —(C₁–C₆)alkyl, —(C₁–C₆)alkyl substituted with one to thirteen halogens selected from fluorine, chlorine, bromine and iodine, phenyl, benzyl, —(C₂–C₆)alkenyl, —(C₃–C₆)cycloalkyl, and —(C₁–C₆)alkoxy;

each and every R³ and R⁴ is independently selected from a group consisting of hydrogen, methyl, ethyl, n-propyl, and i-propyl; or a diastereomeric or optical isomers thereof; or a pharmaceutically acceptable salt thereof;

in combination with a radioactive agent, and detecting the emissions of the radioactive agent.

In another embodiment, the compound of formula I of the methods of the invention is wherein Ar is phenyl, naphthyl, benzoxazolonyl, indolyl, indolonyl, benzimidazolyl, or quinolyl; Ar¹ is phenyl, pyridinyl, pyridazinyl, pyrimidinyl, or pyrazinyl; A is O, S, SO₂, CHOH, or CH₂, preferably O, S, or CH₂; n is 0 or 1; and wherein Ar and Ar¹ are independently and optionally substituted with up to three substituents independently selected from the group consisting of fluoro, chloro, nitro, cyano, —NR¹R², —(C₁–C₆) alkoxy, —COOR, —CONR¹R², and —(C₁–C₆)alkyl. In a more specific embodiment, Ar, Ar¹, A, and n are as defined in this paragraph, except for that Ar and Ar¹ are not substituted with nitro.

In another embodiment, the compound of formula I of the methods of the invention is wherein Ar is optionally substituted phenyl; Ar¹ is optionally substituted and is selected from phenyl, pyridinyl, and pyrimidinyl; A is O; and n is 1.

In another embodiment, the compound of formula I of the methods is wherein when A is O, n is 1 and Ar¹ is 5-fluoropyrimidin-2-yl, then Ar may not be p-fluorophenyl.

In another embodiment, the compound of formula I in the methods of the invention is wherein A is O or S, n is 1, and Ar is phenyl or substituted phenyl.

In another embodiment, the compound of formula I in the methods of the invention is wherein A is CH₂, and n is zero, and Ar is benzoxazolonyl or substituted benzoxazolonyl.

In another embodiment, the compound of formula I of the methods is wherein A is O, Ar is cyanophenyl, and Ar¹ is chloropyridinyl or fluoropyrimidinyl.

In another embodiment, the compound of formula I of the methods is wherein Ar¹ is 5-fluroro-pyrimidin-2-yl.

In another embodiment of the methods, Ar¹ is 5-fluoro-pyrimidin-2-yl or pyrimidin-2-yl.

In another embodiment, the compound of formula I in the methods of the invention is selected from:

(7S,9aS)-7-((3-Methyl-phenoxy)methyl-2-(5-fluoropyrimidin-2-yl)-2,3,4,6,7,8,9,9a-octahydro-1H-pyrido[1,2-a]pyrazine;

(7S,9aS)-7-(3-carbomethoxy-phenoxy)methyl-2-(5-fluoropyrimidin-2-yl)-2,3,4,6,7,8,9,9a-octahydro-1H-pyrido[1,2-a]pyrazine;

(7S,9aS)-7-(3-nitro-phenoxy)methyl-2-(5-fluoropyrimidin-2-yl)-2,3,4,6,7,8,9,9a-octahydro-1H-pyrido[1,2-a]pyrazine;

(7S,9aS)-7-(3-cyano-phenoxy)methyl-2-(5-fluoropyrimidin-2-yl)-2,3,4,6,7,8,9,9a-octahydro-1H-pyrido[1,2-a]pyrazine;

(7S,9aS)-7-(3-methoxy-phenoxy)methyl-2-(5-fluoropyrimidin-2-yl)-2,3,4,6,7,8,9,9a-octahydro-1H-pyrido[1,2-a]pyrazine;

(7S,9aS)-7-(3-acetamido-phenoxy)methyl-2-(5-fluoropyrimidin-2-yl)-2,3,4,6,7,8,9,9a-octahydro-1H-pyrido[1,2-a]pyrazine;

(7S,9aS)-7-(3-(1,1-dimethyl)ethyl-phenoxy)methyl-2-(5-fluoropyrimidin-2-yl)-2,3,4,6,7,8,9,9a-octahydro-1H-pyrido[1,2-a]pyrazine;

and pharmaceutically acceptable salts thereof.

DETAILED DESCRIPTION OF THE INVENTION

The term "treating", as used herein, refers to retarding or reversing the progress of, or alleviating or preventing either the disease, disorder or condition to which the term "treating" applies, or one or more symptoms of such disorder or condition. The term "treatment", as used herein, refers to the act of treating a disorder or condition, as the term "treating" is defined above.

The terms "disease" and "condition", unless otherwise indicated, encompass both chronic diseases and conditions, as well and diseases and conditions that are temporary in nature. A disease or condition treatable according to this invention can be one of sudden onset. A disease or condition covered by the present invention can be genetic and/or environmental in origin. The origin of the disease or condition need not, however, be known, so long as a subject afflicted with the disease or condition can benefit from treatment with one or more compounds described herein.

The term "disorders of the serotonin system", as referred to herein, refers to disorders, the treatment of which can be effected or facilitated by altering (i.e., increasing or decreasing) serotonin mediated neurotransmission.

The term "disorders of the dopamine system", as referred to herein, refers to disorders, the treatment of which can be effected or facilitated by altering (i.e., increasing or decreasing) dopamine mediated neurotransmission.

A "disease or condition caused by a disorder of the serotonin system or a disorder of the dopamine system" is, for purposes of this application, any disease or condition that has at least serotonin mediated neurotransmission or dopamine mediated neurotransmission as a contributing factor. The disease or condition can have, but does not necessarily have, both serotonin mediated neurotransmission and dopamine mediated neurotransmission as contributing factors.

When a disease or condition is said herein to be "caused" by a disorder of the serotonin system or a disorder of the dopamine system, this means that the disorder is a contributing factor to the disease or condition. The disorder need not be the sole factor causing the disease or condition.

The chemist of ordinary skill will recognize that certain combinations of substituents may be chemically unstable and will avoid these combinations or alternatively protect sensitive groups with well known protecting groups.

The term "alkyl", as used herein, unless otherwise indicated, includes saturated monovalent hydrocarbon radicals having straight, branched or cyclic moieties or combinations thereof.

The term "alkoxy", as used herein, unless otherwise indicated, refers to radicals having the formula —O-alkyl, wherein "alkyl" is defined as above.

The compounds of formula I above contain chiral centers and therefore exist in different enantiomeric forms. This invention relates to all optical isomers and all other stereoisomers of compounds of the formula I and mixtures thereof.

This invention also relates to a method of treating a disorder or condition that can be treated by altering (i.e., increasing or decreasing) serotonin mediated neurotransmission in a mammal, including a human, comprising administering to said mammal an amount of a compound of the formula I, as defined above, or a pharmaceutically acceptable salt thereof, that is effective in treating such disorder or condition.

Examples of depression that can be treated according to the invention described herein include, but are not limited to, dysthymia, major depressive disorder, pediatric depression, recurrent depression, single episode depression, post partum depression, depression in Parkinson's patients, cancer patients, and post myocardial infarction patients, and sub-syndromal symptomatic depression. Examples of phobias that can be treated according to the invention described herein include, but are not limited to, social phobia, agoraphobia, and specific phobias.

Examples of eating disorders that can be treated according to the invention herein include, but are not limited to, bulimia and anorexia nervosa.

Examples of chemical dependency and/or addiction treatable according to the invention described herein include, but are not limited to, dependency on, and/or addiction to, alcohol, nicotine, cocaine, heroin, phenolbarbitol or a benzodiazepine.

Examples of sexual disorders that can be treated according to the invention described herein include, but are not limited to, paraphilias, premature ejaculation, and sexual dysfunction.

This invention also relates to any of the foregoing methods, wherein the compound of the formula I, as defined above, or pharmaceutically acceptable salt thereof, is administered in combination with a serotonin reuptake inhibitor (SRI) (e.g., sertraline, fluoxetine, fenfluramine, or fluvoxamine). The term "administered in combination with", as used herein, means that the compound of formula I or pharmaceutically acceptable salt thereof is administered in the form of a pharmaceutical composition that also contains an SRI, or that such compound or salt is administered in a separate pharmaceutical composition from that in which the SRI is administered, but as part of a dose regimen that calls for the administration of both active agents for treatment of a particular disorder or condition.

This invention also relates to the above method of treating cerebral infarct such as that caused by stroke, ischemia or traumatic head injury in a mammal, wherein the compound of the formula I, as defined above, or pharmaceutically acceptable salt thereof, is administered in combination with a serotonin-2 ($5HT_2$) receptor antagonist (e.g., ketanserin, pelanserin, pipamperone, spiperone, pirenperin or ritanserin) or a pharmaceutically acceptable salt thereof. Other $5HT_2$ receptor antagonists that can be used in the methods of this invention are referred to in U.S. Pat. No. 5,364,857, which issued on Nov. 15, 1994. This patent is incorporated herein by reference in its entirety.

The pharmaceutically acceptable acid addition salts of compounds of the formula I may be used, as referred to above, in the various methods of this invention. The compounds of formula I are basic in nature and are capable of forming a wide variety of salts with various inorganic and organic acids. The acids that may be used to prepare pharmaceutically acceptable acid addition salts of those compounds of formula I are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isohicotinate, acetate, lactate, salicylate, citrate, acid citrate, tartrate, pantothenate, bitartrate, ascorbate, succinate, maleate, fumarate, gluconate, glucaronate, saccharate, formate, benzoate, glutamate, methanesulfonate, ethanesulfonate, benzenesulfonate, and p-toluenesulfonate.

The term "one or more substituents", as used herein, includes from one to the maximum number of substituents possible based on the number of available bonding sites.

Formula I above includes compounds identical to those depicted but for the fact that one or more atoms (for example, hydrogen, carbon or fluorine atoms) are replaced by radioactive isotopes thereof. Such radiolabelled compounds are useful as research and diagnostic tools in, for example, metabolism studies, pharmokinetic studies and binding assays.

This invention also relates to a method, such as positron emission tomography (PET), of obtaining images of a mammal, including a human, to which a radiolabelled compound of the formula I, or pharmaceutically acceptable salt thereof, has been administered.

The compounds of formula I that are employed in the present invention, being ligands for serotonin receptor subtypes, especially the $5HT_{1A}$ receptor, within the body, are accordingly of use in the treatment of disorders of the serotonin system.

The compounds of formula I and their pharmaceutically acceptable salts (hereinafter also referred to, collectively, as "the therapeutic compounds used in the methods of this invention") can be prepared as described in U.S. application Ser. No. 08/809,145, now U.S. Pat. No. 5,852,031, supra, incorporated herein in its entirety by reference.

Compounds of formula I in which one or more atoms are radioactive may be prepared by methods known to a person of ordinary skill in the art.

For example, compounds of formula I wherein the radioactive atom is tritium may be prepared by reacting an aryl halide Ar—X, wherein the halogen is chlorine, bromine or iodine, with gaseous $^3H_2$ and a nobel metal catalyst, such as palladium suspended on carbon, in a suitable solvent such as a lower alcohol, perferably methanol or ethanol. Compounds of formula I wherein the radioactive atom is $^{18}F$ may be prepared by reacting an aryl trialkyl stannane Ar—SnR$_3$, wherein R is lower alkyl, preferably methyl or n-butyl, with $^{18}F$-enriched fluorine (F$_2$), OF$_2$ or CF$_2$OOF in a suitably inert solvent (cf M. Namavari, et at., *J. Fluorine Chem.,* 1995, 74, 113).

Compounds of formula I wherein the radioactive atom is $^{11}C$ or $^{14}C$ may be prepared by reacting an aryl halide Ar—X, wherein X is preferably bromine or iodine, or an aryl trifluoromethane sulfonate (Ar—OSO$_2$CF$_3$) with potassium [$^{11}C$]cyanide or potassium [$^{14}C$]cyanide and a nobel metal catalyst, preferably tetrakis(triphenylphosphine)palladium, in a reaction inert solvent such water or tetrahydrofuran, and preferably a mixture of water and tetrahydrofuran. (See Y. Andersson, B. Langstrom, *J. Chem. Soc. Perkin Trans.* 1, 1994, 1395).

The utility of radioactive agents with affinity for 5HT$_{1A}$ receptors for visualizing organs of the body either directly or indirectly has been documented in the literature. For example, C.-Y. Shiue et al., *Synapse,* 1997, 25, 147 and S. Houle et al, *Can. Nucl. Med. Commun,* 1997, 18, 1130, describe the use of 5HT$_{1A}$ receptor ligands to image 5HT$_{1A}$ receptors in the human brain using positron emission tomography (PET). The foregoing references are incorporated herein by reference in their entireties.

The therapeutic compounds used in the methods of this invention can be administered orally, buccally, transdermally (e.g., through the use of a patch), parenterally or topically. Oral administration is preferred. In general, these compounds are most desirably administered in dosages ranging from about 1 mg to about 1000 mg per day, although variations may occur depending on the weight and condition of the person being treated and the particular route of administration chosen. In some instances, dosage levels below the lower limit of the aforesaid range may be more than adequate, while in other cases still larger doses may be employed without causing any harmful side effect, provided that such larger doses are first divided into several small doses for administration throughout the day.

When used in the same oral, parenteral or buccal pharmaceutical composition as an SRI, the daily dose of the compound of formula I or pharmaceutically acceptable salt thereof will be within the same general range as specified above for the administration of such compound or salt as a single active agent. The daily dose of the SRI in such a composition will generally be within the range of about 1 mg to about 400 mg.

When used in the same oral, parenteral or buccal pharmaceutical composition as a 5HT$_2$ antagonist, the daily dose of the compound of formula I or pharmaceutically acceptable salt thereof will be within the same general range as specified above for the administration of such compound, or salt as a single active agent. The daily dose of the 5HT$_2$ antagonist in such a composition will generally be within the range of about 0.1–10 parts by weight, relative to 1.0 part by weight of the compound formula I.

The therapeutic compounds used in the methods of this invention may be administered alone or in combination with pharmaceutically acceptable carriers or diluents by either of the two routes previously indicated, and such administration may be carried out in single or multiple doses. More particularly, the therapeutic compounds used in the methods of this invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, elixirs, syrups, and the like. Such carriers include solid diluents or fillers, sterile aqueous media and various non-toxic organic solvents, for example. Moreover, oral pharmaceutical compositions can be suitably sweetened and/or flavored.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a therapeutic compound used in the methods of the present invention in either sesame or peanut oil or in aqueous propylene glycol may be employed. The aqueous solutions should be suitably buffered if necessary and the liquid diluent first rendered isotonic. These aqueous solutions are suitable for intravenous injection purposes. The oily solutions are suitable for intra-articular, intramuscular and subcutaneous injection purposes. The preparation of all these solutions under sterile conditions is readily accomplished by standard pharmaceutical techniques well known to those skilled in the art.

Additionally, it is also possible to administer the therapeutic compounds used in the methods of the present invention topically when treating inflammatory conditions of the skin and this may preferably be done by way of creams, jellies, gels, pastes, ointments and the like, in accordance with standard pharmaceutical practice.

The activity of the compounds of the present invention with respect to 5HT$_{1A}$ binding ability can be determined according to the following procedure. Binding assays using membranes derived from HeLa cells expressing the human 5HT$_{1A}$ receptor or from membranes derived from rat brain tissue can be performed according to standard procedures. For example, HeLa cells expressing the human 5HT$_{1A}$ receptor can be grown in culture to confluence and then harvested by replacing the media with phosphate-buffered saline containing 5 mM EDTA and centrifuging at 1000×g for 10 minutes at 4° C. The pellet is homogenized in a 50 mM Tris buffer containing 4 mM CaCl$_2$ and having a pH of 7.7, using a Brinkman Polytron at setting 6 for 20 seconds and centrifuged at 48,000×g for 10 minutes at 4° C. Membranes are stored frozen at −78° C. until the time of assay. On the day of the experiment, the membranes are resuspended in a 50 mM Tris buffer (pH 7.7) containing 4 mM CaCl$_2$ and 10 μM pargyline to a final tissue concentration of 2.5 mg/mL and added to test tubes containing an incubation buffer, various concentrations of test drug, and [$^3$H]-8-OH-DPAT. Non-specific binding is defined in the presence of a saturating concentration of 5HT. Assay tubes are incubated for 30 minutes at 37° C. to attain equilibrium, and incubations are terminated by rapid filtration through Whatman GF/B filters using a Brandel cell harvester. The membranes are washed three times with 4 mL aliquots of an ice-cold buffer (without CaCl$_2$ or pargyline). Membrane-bound ligand is determined by liquid scintillation counting of the filters in Ready-Safe scintillation cocktail. The dissociation constant ($K_d$) for the radioligand, previously determined by saturation analysis, is used to calculate apparent $K_i$'s by means of the Cheng-Prusoff equation (Cheng and Prusoff, 1973). The IC$_{50}$ concentrations (concentration of compound required to displace specific binding by 50%) can be calculated by linear regression analysis of the concentration-response curves from competition binding studies. The preferred compounds of this invention bind to the human 5HT$_{1A}$ receptor with a $K_i$ less than 5.0 micromolar.

The agonist and antagonist activities of the therapeutic compounds used in the methods of this invention at 5-HT$_{1A}$ receptors can be determined using a single saturating concentration according to the following procedure. Male Hartley guinea pigs are decapitated the brain removed and the hippocampus is dissected out. The hippocampus is homogenized in a 5 mM HEPES buffer containing 1 mM EGTA (pH 7.5) using a hand-held glass-Teflon® homogenizer and centrifuged at 35,000×g for 10 minutes at 4° C. The pellets are resuspended in a 100 mM HEPES buffer containing 1 mM EGTA (pH 7.5) to a final protein concentration of 20 ug of protein per tube. The following agents are added so that the reaction mix in each tube contained 2.0 mM MgCl$_2$, 0.5 mM ATP, 1.0 mM cAMP, 0.5 mM IBMX, 10 mM phosphocreatine, 0.31 mg/mL creatine phosphokinase, 100 μM GTP and 0.5–1 microcuries of [$^{32}$P]-ATP (30 Ci/mmol: NEG-003—New England Nuclear). Incubation is initiated by the addition of tissue to siliconized microfuge tubes (in triplicate,) at 30° C. for 15 minutes. Each tube receives 20 μL tissue, 10 μL drug or buffer (at 10× final concentration), 10 μL 32 nM agonist or buffer (at 10× final concentration), 20 μL forskolin (3 μM final concentration) and 40 μL of the preceding reaction mix. Incubation is terminated by the addition of 100 mL 2% SDS, 1.3 mM cAMP, 45 mM ATP solution containing 40,000 dpm [$^3$H]-cAMP (30 Ci/mmol: NET-275—New England Nuclear) to monitor the recovery of cAMP from the columns. The separation of [$^{32}$P]-ATP and [$^{32}$P]-cAMP is accomplished using the method of Salomon et al., *Analytical Biochemistry*, 1974, 58, 541–548. Radioactivity is quantified by liquid scintillation counting. Maximal inhibition is defined by 10 μM (R)-8-OH-DPAT for 5-HT$_{1A}$ receptors. Percent inhibition by the test compounds is then calculated in relation to the inhibitory effect of (R)8-OH-DPAT for 5-HT$_{1A}$ receptors. The reversal of agonist induced inhibition of forskolin-stimulated adenylate cyclase activity is calculated in relation to the 32 nM agonist effect.

The dopaminergic activity of the compounds of formula I, in particular their D$_4$ receptor binding ability, can be determined as described in U.S. application Ser. No. 08/809,145, now U.S. Pat. No. 5,852,031, supra.

The following Examples of therapeutic compounds of formula I useful in the present invention are provided solely for the purposes of illustration and do not limit the invention which is defined by the claims.

EXAMPLE 1

(7R,9aS)-7-(Phenoxy)methyl-(2-pyrimidin-2-yl)-2,3,4,6,7,8,9,9a-octahydro-1H-pyrido[1,2-a]pyrazine

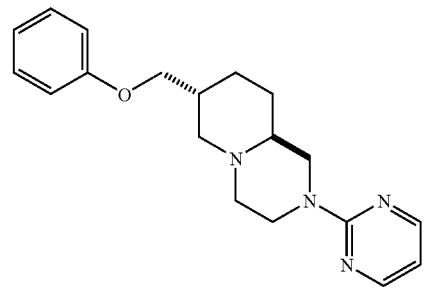

A solution of 0.385 g (1.55 mmol) of (7R,9aS)-7-hydroxymethyl-2-(pyrimidin-2-yl)-2,3,4,6,7,8,9,9a-octahydro-1H-pyrido[1,2-a]pyrazine (Preparation 4), 0.220 g (2.34 mmol) of phenol, and 0.488 g (1.86 mmol) of triphenylphosphine in 30 mL of dry THF was treated with 0.324 g (1.86 mmol) of diethyl azodicarboxylate, and the mixture stirred at 23° C. for 16 h. The solvent was evaporated, the residue dissolved in ethyl ether and treated with HCl(g) in ether. The precipitate was collected on a Büchner funnel, and washed with 1:1 ether:ethyl acetate three times. The solid was dissolved in water, basified with 1 M NaOH and extracted with chloroform. The organic layer was washed with 1 M NaOH (2×) and water (1×), dried (magnesium sulfate), filtered and evaporated to give 0.310 g of (7R,9aS)-7-phenoxymethyl-2,3,4,6,7,8,9,9a-octahydro-2-pyrimidin-2-yl-1H-pyrido[1,2-a]pyrazine. mp (.HCl) 203–205° C. $^{13}$C NMR (base, CDCl$_3$): δ 27.0, 29.0, 36.4, 43.6, 49.1, 54.9, 58.8, 60.8, 70.9, 109.8, 114.5, 120.6, 129.4, 157.7, 159.0, 161.5. HRMS calcd for C$_{19}$H$_{24}$N$_4$O: 324.195. Found: 324.194.

EXAMPLE 2

7-(Substituted-phenoxy)methyl-2-(pyrimidin-2-yl)-2,3,4,6,7,8,9,9a-octahydro-1H-pyrido[1,2-a]pyrazines

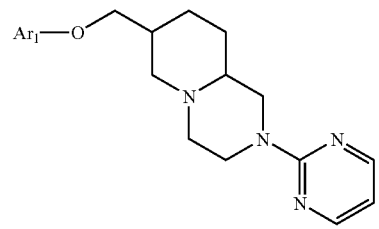

Compounds of the above formula were prepared from isomers of 7-hydroxymethyl-(2-pyrimidin-2-yl)-2,3,4,6,7,8,9,9a-octahydro-1H-pyrido[1,2-a]pyrazine (Preparation 4, U.S. Pat. No. 5,122,525, and WO92/13858) according to Example 1, substituting the appropriate phenol. Purification was generally accomplished by flash silica gel chromatography using mixtures of ethyl acetate and hexane or mixture of chloroform and methanol as the eluting solvent. The stereo-chemical configuration, 7-(optionally substituted phenoxy)methyl substituent, melting point of the monohydrochloride salt, and high resolution mass spectral data are shown. U.S. Pat. No. 5,122,525 is hereby incorporated in its entirety into this application by reference.

EXAMPLE 2a (7SR,9aSR)-7-Phenoxymethyl; mp 119–122° C.; Anal calcd for $C_{19}H_{24}N_4O \cdot HCl$: C, 63.23; H, 6.98; N, 15.53. Found: C, 63.19; H, 7.30; N, 15.66.

EXAMPLE 2b (7R,9aR)-7-Phenoxymethyl; mp 226–231° C.; HRMS calcd for $C_{19}H_{24}N_4O$: 324.1945, found: 324.1920.

EXAMPLE 2c (7RS,9aSR)-7-(4-Fluorophenoxy)methyl; mp 263–266° C.; HRMS calcd for $C_{19}H_{23}FN_4O$: 342.1851, found: 342.1796.

EXAMPLE 2d (7RS,9aSR)-7-((2,4-Difluoro)phenoxymethyl); mp 242.5–244° C.; HRMS calcd for $C_{19}H_{22}F_2N_4O$: 360.1762, found: 360.1775.

EXAMPLE 2e (7RS,9aSR)-7-(3,4-Difluorophenoxy)methyl; mp 239–240° C.; HRMS calc for $C_{19}H_{22}F_2N_4O$: 360.1762, found: 360.1745.

EXAMPLE 2f (7RS,9aSR)-7-((3-Fluoro)phenoxymethyl); mp 242–243° C.; HRMS calc for $C_{19}H_{23}FN_4O$: 342.1856, found: 342.1851.

EXAMPLE 2g (7RS,9aSR)-7-(2-Naphthoxymethyl); mp 143–145° C.; HRMS calc for $C_{23}H_{26}N_4O$: 374.2107, found: 374.2097.

EXAMPLE 2h (7RS,9aSR)-7-(1-Naphthoxymethyl); mp 243–245° C.; HRMS calcd for $C_{23}H_{26}N_4O$: 374.2107, found: 374.2098.

EXAMPLE 2i (7RS,9aSR)-7-(4-Fluoro-3-methylphenoxy)methyl; mp 232–233° C.; HRMS calc for $C_{20}H_{25}FN_4O$: 356.2012, found: 356.1992.

EXAMPLE 2j (7RS,9aSR)-7-((3-Carbomethoxy)phenoxymethyl); mp 194–196° C.; HRMS calc for $C_{21}H_{26}N_4O_3$: 382.2005, found: 382.2010.

EXAMPLE 2k (7RS,9aSR)-7-(5-Fluoroquinolin-8-yloxy)methyl; mp 218–220° C.; HRMS calc for $C_{22}H_{25}FN_5O$ (MH+): 394.2043, found: 394.2059

EXAMPLE 2l (7RS,9aSR)-7-((2-Methoxy-5-(1-methyl)ethyl)phenoxy)methyl; mp 94–99° C.; HRMS calcd for $C_{23}H_{32}N_4O_2$: 396.2518, found: 396.2504.

EXAMPLE 2m (7RS,9aSR)-7-((2-Methoxy-3-(1-methyl)ethyl)phenoxy)methyl; mp 219–221° C.; HRMS calcd for $C_{23}H_{32}N_4O_2$: 396.2518, found: 396.2522.

EXAMPLE 2n (7RS,9aSR)-7-((2-Methoxy-4-acetyl)phenoxy)methyl; mp 224° C. (dec); HRMS calcd for $C_{22}H_{28}N_4O_3$: 396.215, found: 396.210.

EXAMPLE 2o (7R,9aS)-7-(3-(1-Methyl)ethylphenoxy)methyl; mp 70–120° C. (dec); HRMS calcd for $C_{22}H_{30}N_4O$: 366.2413, found: 366.2420.

EXAMPLE 2p (7R,9aS)-7-((2-Methoxy)phenoxy)methyl; mp 213–215° C.; HRMS calcd for $C_{20}H_{26}N_4O_2$: 354.2050. found: 354.2093.

EXAMPLE 2q (7R,9aS)-7-((4-Acetamido)phenoxy)methyl; mp 192° C.; HRMS calcd for $C_{21}H_{27}N_5O_2$: 381.2159, found: 381.2120.

EXAMPLE 2r (7R,9aS)-7-(4-(1,1-Dimethyl)ethyl-phenoxy)methyl; mp 237–244° C. (dec); HRMS calcd for $C_{23}H_{32}N_4O$: 380.2576, found: 380.2674.

EXAMPLE 2s (7R,9aS)-7-(3-(1,1-Dimethyl)ethyl-phenoxy)methyl; mp 229–230° C.; HRMS calcd for $C_{23}H_{32}N_4O$: 380.2576, found: 380.2577.

EXAMPLE 2t (7R,9aS)-7-(2-(1,1-Dimethyl)ethyl-phenoxy)methyl; mp 240–241° C.; HRMS calcd for $C_{23}H_{32}N_4O$: 380.2576, found: 380.2580.

EXAMPLE 2u (7R,9aS)-7-(4-Methoxy-phenoxy)methyl; mp 219–222° C.; HRMS calcd for $C_{20}H_{26}N_4O_2$: 354.2050, found: 354.2063.

EXAMPLE 2v (7R,9aS)-7-(3-Methoxy-phenoxy)methyl; mp 113–115° C.; HRMS calcd for $C_{20}H_{26}N_4O_2$: 354.2056, found: 354.2041.

EXAMPLE 2w (7R,9aS)-7-(3-Acetamido-phenoxy)methyl; mp 156–158° C.; HRMS calcd for $C_{21}H_{27}N_5O_2$: 381.2165, found: 381.2160.

EXAMPLE 2x (7R,9aS)-7-(2-Cyano-phenoxy)methyl; mp 250–252° C.; HRMS calcd for $C_{20}H_{23}N_5O$: 349.1903, found: 349.1932.

EXAMPLE 2y (7R,9aS)-7-(3-Cyano-phenoxy)methyl; mp 241.5–243° C.; HRMS calcd for $C_{20}H_{23}N_5O$: 349.1903, found: 349.1897.

EXAMPLE 2z (7R,9aS)-7-(3-Dimethylamino-phenoxy)methyl; mp 80–82° C.; HRMS calcd for $C_{21}H_{29}N_5O$: 367.2372, found: 367.2357.

EXAMPLE 2aa (7R,9aS)-7-(3,4-Difluoro-phenoxy)methyl; mp 252–254° C.; HRMS calcd for $C_{19}H_{22}F_2N_4O$: 360.1762, found: 360.1763.

EXAMPLE 2ab (7S,9aR)-7-(4-Fluoro-phenoxy)methyl; mp 281–282° C.; HRMS calcd for $C_{19}H_{23}FN_4O$: 342.1856, found: 342.1841.

EXAMPLE 3

(7R,9aS)-7-(Substituted)methyl-2-(5-fluoropyrimidin-2-yl)-2,3,4,6,7,8,9,9a-octahydro-1H-pyrido[1,2-a]pyrazines

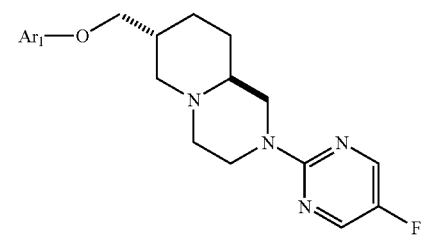

Compounds of the above formula were prepared according to Example 1 using (7R,9aS)-7-hydroxymethyl-2-(5-fluoropyrimidin-2-yl)-2,3,4,6,7,8,9,9a-octahydro-1H-pyrido[1,2-a]pyrazine (Preparation 5) and the appropriate phenol. Purification was generally accomplished by flash silica gel chromatography using mixtures of ethyl acetate and hexane or mixtures of chloroform and methanol as the eluting solvent. The stereochemical configuration, 7-substituent, melting point of the monohydrochloride salt and HRMS or $^{13}C$ NMR data are shown.

EXAMPLE 3a (7R,9aS)-7-(3-Cyanophenoxy)methyl; mp 192–194° C.; HRSM calcd for $C_{20}H_{22}FN_5O$: 367.1808, found: 367.1821.

EXAMPLE 3b (7R,9aS)-7-(4-Cyanophenoxy)methyl; mp 256–257° C.; HRSM calcd for $C_{20}H_{22}FN_5O$: 367.1808, found: 367.1793.

EXAMPLE 3c (7R,9aS)-7-(2-Methoxy-3-(1-methyl)ethyl-phenoxy)methyl; mp>286° C.; HRSM calcd for $C_{23}H_{31}FN_4O$: 414.2424, found: 414.2418.

EXAMPLE 3d (7R,9aS)-7-(2-Fluorophenoxy)methyl; mp 209–210° C.; HRSM calcd for $C_{19}H_{22}F_2N_4O$: 360.1762, found: 360.1767.

EXAMPLE 3e (7R,9aS)-7-(3-Fluorophenoxy)methyl; mp 229–232° C.; HRSM calcd for $C_{19}H_{22}F_2N_4O$: 360.1767. found: 360.1755.

EXAMPLE 3f (7R,9aS)-7-(4-Fluorophenoxy)methyl; mp 249–254° C.; HRSM calcd for $C_{19}H_{22}F_2N_4O$: 360.1767, found: 360.1741.

EXAMPLE 3g (7R,9aS)-7-(3,4-Difluorophenoxy)methyl; mp 229–236° C.; HRMS calcd. for $C_{19}H_{21}F_3N_4O$: 378.1667, found: 378.1660.

EXAMPLE 3h (7R,9aS)-7-(3,5-Difluorophenoxy)methyl; mp 248–250° C.; HRSM calcd for $C_{19}H_{21}F_3N_4O$: 378.1667, found: 378.1680.

EXAMPLE 3i (7R,9aS)-7-(4-Iodophenoxy)methyl; mp 284–286° C.; HRMS calcd for $C_{19}H_{22}FIN_4O$: 468.0822. found: 468.0785.

EXAMPLE 4

(7RS,9aSR)-7-Phenoxymethyl-2-(5-fluoro-4-thiomethylpyrimidin-2-yl)-2,3,4,6,7,8,9,9a-octahydro-1H-pyrido[1,2-a]pyrazine

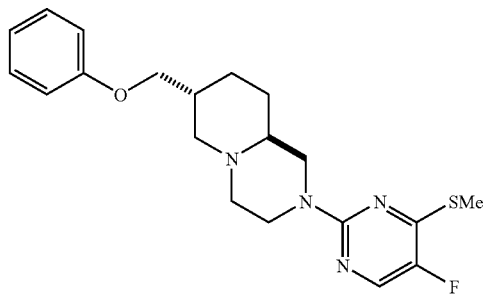

The title compound was prepared according to Example 1 using phenol and (7RS,9aSR)-7-hydroxymethyl-2-(5-fluoro-4-thiomethyl) pyrimidin-2-yl)-2,3,4,6,7,8,9,9a-octahydro-1H-pyrido[1,2-a]pyrazine (Preparation 6). mp (.HCl) 192–198° C. Anal calcd for $C_{20}H_{25}FN_4OS$: C, 61.82; H, 6.49; N, 14.42. Found: C, 61.52; H, 6.56; N, 14.42.

EXAMPLE 5

(7RS,9aSR)-7-Phenoxymethyl-2-(5-fluoropyrimidin-2-yl)-2,3,4,6,7,8,9,9a-octahydro-1H-pyrido[1,2-a]pyrazine

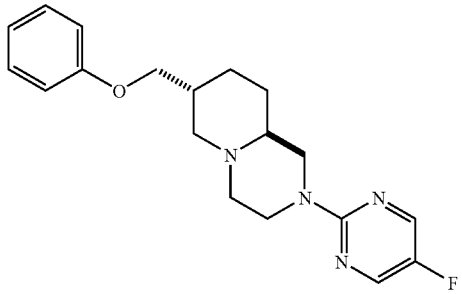

A solution of 3.74 g (9.63 mmol) of (7RS,9aSR)-7-phenoxymethyl-2-(5-fluoro4-thiomethylpyrimidin-2-yl)-2,3,4,6,7,8,9,9a-octahydro-1H-pyrido[1,2-a]pyrazine (Example 4) in 200 mL of ethanol was treated with 0.3 g of Raney nickle and the mixture was refluxed for 2 h. An additional 0.3 g of catalyst was added and reflux continued for 24 h. A third quantity of catalyst (0.3 g) was added and reflux continued for another 24 h. A fourth quantity of catalyst (0.3 g) was added and refluxed for 4 h. The mixture was cooled to room temperature, filtered through Celite, washing with ethanol and the filtrate was evaporated. Purification by flash silica gel chromatography with methylene chloride and 99:1 methylene chloride:methanol gave 1.30 g (39%) of the title compound. mp (.HCl) 215–217° C. HRMS calcd for $C_{19}H_{23}FN_4O$: 342.1851, found: 342.1853.

EXAMPLE 6

(7RS,9aSR)-7-(4-Fluorophenoxy)methyl-2-(5-fluoro-4-thiomethyl-pyrimidin-2-yl)-2,3,4,6,7,8,9,9a-octahydro-1H-pyrido[1,2-a]pyrazine

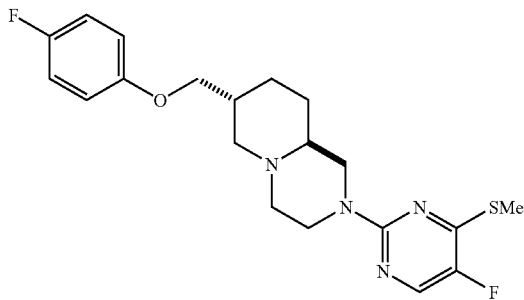

The title compound was prepared according to Example 1 using 4-fluorophenol and (7RS,9aSR)-7-hydroxymethyl-2-(5-fluoro-4-thiomethylpyrimidin-2-yl)-2,3,4,6,7,8,9,9a-octahydro-1H-pyrido[1,2-a]pyrazine (Preparation 6). mp (.HCl) 201–210° C. $^{13}$C NMR (base, CDCl$_3$): δ 11.5, 27.0, 29.0, 36.4, 44.3, 49.8, 54.8, 58.8, 60.7, 71.6, 115.35, 115.45, 115.59, 115.90, 140.4, 140.7, 150.9, 155.1, 158.8. HRSM calcd for $C_{20}H_{24}F_2N_4OS$: 406.166, found: 406.161.

EXAMPLE 7

(7RS,9aSR)-7-(4-Fluorophenyl)methyl-2-(5-fluoropyrimidin-2-yl)-2,3,4,6,7,8,9,9a-octahydro-1H-pyrido[1,2-a]pyrazine

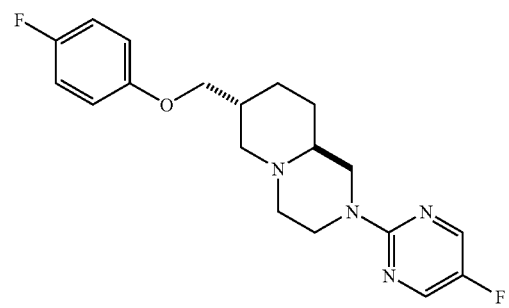

Using the procedure described in Example 5, 8.23 g (20.3 mmol) of (7RS,9aSR)-7-(4-fluorophenoxy)methyl-2-(5-fluoro-4-thiomethylpyrimidin-2-yl)-2,3,4,6,7,8,9,9a-octahydro-1 H-pyrido[1,2-a]pyrazine gave 3.4 g of the title compound. mp (.HCl) 249–253° C. Anal calcd for $C_{19}H_{22}F_2N_4O$·HCl: C, 57.50; H, 5.84; N, 14.12; found: C, 57.40; H, 5.84; N,13.99.

EXAMPLE 8

(7SR,9aSR)-7-((4-Fluorophenoxy)methyl)-2-(pyrimidin-2-yl)-2,3,4,6,7,8,9,9a-octahydro-1H-pyrido[1,2-a]pyrazine

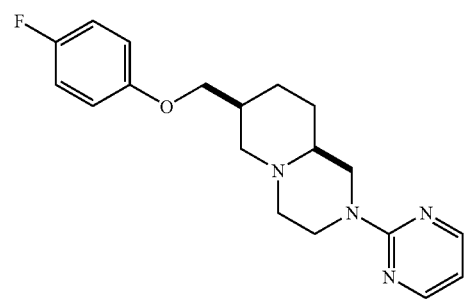

A solution of 0.600 g (2.43 mmol) of (7SR,9aSR)-7-hydroxymethyl-2-(pyrimidin-2-yl)-2,3,4,6,7,8,9,9a-octahydro-1H-pyrido[1,2-a]pyrazine (U.S. Pat. No. 5,122,525) and 0.34 mL (2.7 mmol) of triethylamine in 10 mL of methylene chloride at 0° C. was treated with 0.20 mL (2.5 mmol) of methanesulfonyl chloride. After 10 min, the mixture was diluted with water, basified with 1 M NaOH, separated, and the mixture was extracted with more methylene chloride (2×). The combined organic layers were washed with water (1×), dried (magnesium sulfate), filtered, and evaporated to give 0.77 g (2.6 mmol) of mesylate.

A solution of 0.82 g (7.3 mmol) of 4-fluorophenol in 8 mL of DMF was treated with 0.35 g (8.8 mmol) of sodium hydride (60% oil dispersion) and allowed to react for 2 h at 40–50° C. The reaction mixture was cooled to room temperature and a solution of 0.77 g (2.6 mmol) of the above mesylate in 8 mL of DMF was added. The reaction was then heated at 100° C. for 16 h. After cooling to room temperature, the solvent was evaporated, the residue taken up in water, the pH adjusted to 2 with 1 M HCl, and washed with ethyl acetate. The aqueous phase was made basic (pH 11) with 1 M NaOH and extracted with ethyl acetate (3×). The combined organic layers were dried (magnesium sulfate), filtered, and evaported to give 0.430 g of crude product. Purification by silica gel flash chromatography eluting with 90:10 ethyl acetate:hexane gave 0.340 g (38%) of the title compound. A salt was prepared by mixing an ethanol-ethyl acetate solution of 0.29 g free base with a solution of 98 mg of maleic acid in ethanol and evaporating to dryness. The white solid was triturated with ether and dried in vacuo to give 0.35 g of salt. mp (.$C_4H_4O_4$) 128–139° C. $^{13}$C NMR (base, CDCl$_3$): δ 24.8, 25.2, 33.8, 43.6, 49.1, 54.9, 56.6, 61.1, 69.5, 109.7, 115.48, 115.25, 115.58, 115.83, 155.4, 157.7, 161.5. Anal. calcd for $C_{19}H_{23}N_4OF$: C, 66.64; H, 6.77; N, 16.36. Found: C, 66.28; H, 7.02; N, 16.45.

EXAMPLE 9

(7RS,9aSR)-7-Phenoxymethyl-2-(pyrimidin-2-yl)-2,3,4,6,7,8,9,9a-octahydro-1H-pyrido[1,2-a]pyrazine

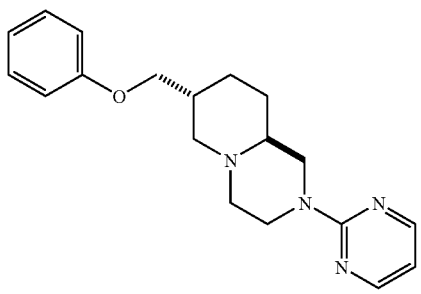

A solution of 1.0 g (4.0 mmol) of (7RS,9aSR)-7-hydroxymethyl-2-(pyrimidin-2-yl)-2,3,4,6,7,8,9,9a-octahydro-1H-pyrido[1,2-a]pyrazine (Preparation 3) in 20 mL dry methylene chloride was cooled to 0° C., and treated with 0.57 mL (4.4 mmol) of triethylamine and 0.33 mL (4.2 mmol) of methanesulfonyl chloride dropwise. After 15 min, water was added and the pH adjusted to 11 with 1N NaOH. The layers were separated and the aqueous phase was extracted with methylene chloride (2×). The combined organic phase was dried (magnesium sulfate), filtered and evaporated to give 1.0 g (76%) of mesylate.

A mixture of 10 mL of DMF, 0.90 g (9.6 mmol) of phenol, and 0.45 g (10.2 mmol) of NaH (60% oil dispersion) in a dry flask was stirred for 1.5 h at 40–50° C. After cooling to room temperature, the, above mesylate was added in 10 mL of DMF, and the solution was heated at 100–110° C. for 16 h. After cooling to room temperature, water was added, the pH adjusted to 11 with 1N NaOH, and the mixture extracted with ethyl acetate (3×), dried (magnesium sulfate), filtered and evaporated. The crude product was triturated with a few mL of water redisolved in ethyl acetate, dried (magnesium sulfate), filtered and evaporated. Flash chromatography on silical gel with ethyl acetate gave 0.68 g of the free base as a white solid. mp (.2HCl) 218–223° C. $^{13}$C NMR (base, CDCl$_3$): δ 27.0, 29.0, 36.4, 43.6, 49.1, 54.9, 58.8, 60.8, 70.9, 109.8, 114.5, 120.6, 129.4, 157.7, 159.0, 161.5. Calcd for $C_{19}H_{24}NO_4$.2HCl: C, 57.43; H; 6.60; N 14.10; found: C, 57.54; H, 6.88; N, 13.83.

EXAMPLE 10

7-(Substitutedphenoxymethyl)-2-(pyrimidin-2-yl)-2,3,4,6,7,8,9,9a-octahydro-1H-pyrido[1,2-a]pyrazines

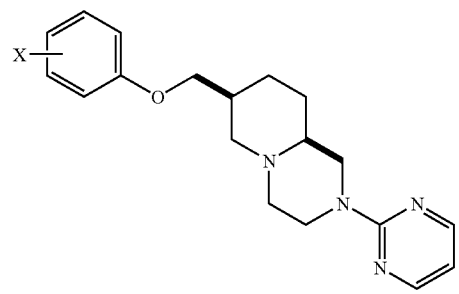

Compounds of the above formula were prepared according to Example 8 from (7SR,9aSR)-7-hydroxymethyl-2-(pyrimidin-2-yl)-2,3,4,6,7,8,9,9a-octahydro-1H-pyrido[1,2-a]pyrazines (U.S. Pat. No. 5,122,525) and the appropriate phenol. Purification was generally accomplished by flash silica gel chromatography using mixtures of ethyl acetate and hexane or mixture of chloroform and methanol as the eluting solvent. The stereochemical configuration, 7-phenoxymethyl substituent, melting point of the monohydrochloride salt and HRMS or combustion analysis or $^{13}$C NMR data are shown.

EXAMPLE 10a (7SR,9aSR)-7-(4-Acetamidophenoxy)methyl; mp 123° C. (dec); $^{13}$C NMR (base, CDCl$_3$): δ 24.3, 24.8, 25.1, 33.7, 43.6, 49.1, 54.8, 56.6, 61.1, 69.1, 109.7, 114.9, 121.9, 130.9, 156.2, 157.7, 161.5, 168.3.

EXAMPLE 10b (7SR,9aSR)-7-((4-Trifluoromethyl)phenoxy)methyl; mp 104–119° C.; HRMS calcd for $C_{20}H_{23}F_3N_4O$: 392.1819, found: 392.1833.

EXAMPLE 10c (7SR,9aSR)-7-((4-Methoxy)phenoxy)methyl; mp 112–114° C.; Anal calcd for $C_{20}H_{26}N_4O_2$.HCl: C, 61.44; H, 6.96; N, 14.33. Found: C, 61.23; H, 7.29; N, 14.51.

EXAMPLE 10d (7SR,9aSR)-7-((4-Carboethoxy)phenoxy)methyl; mp 189–191° C.; HRMS calcd for $C_{22}H_{28}N_4O_3$: 396.2162, found: 396.2179.

EXAMPLE 11

(7R,9aS)-7-(4-Fluorophenoxy)methyl-2-(pyrimidin-2-yl)-2,3,4,6,7,8,9,9a-octahydro-1H-pyrido[1,2-a]pyrazine

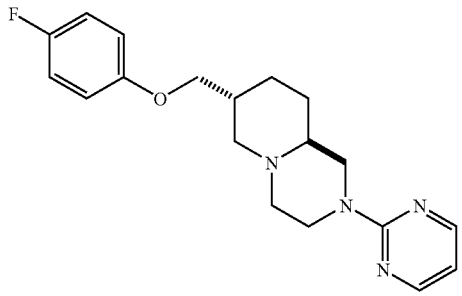

The title compound was prepared according to Preparation 3 with 2-chloropyrimidine and (7R,9aS)-7-(4-fluorophenoxy)methyl-2,3,4,6,7,8,9,9a-octahydro-1H-pyrido[1,2-a]pyrazine (Preparation 8). mp (.HCl) 283–285° C. HRMS calcd for $C_{19}H_{23}FN_4O$: 342.1856; found: 342.1867.

EXAMPLE 12

(7R,9aS)-7-(2-Phenyl)ethyl-2-(5-fluoropyrimidin-2-yl)-2,3,4,6,7,8,9,9a-octahydro-1H-pyrido[1,2-a]pyrazine

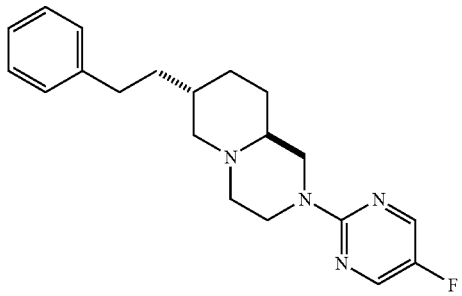

A mixture of 3.75 g (14.1 mmol) of (7R,9aS)-7-hydroxymethyl-2-(5-fluoropyrimidin-2-yl)-2,3,4,6,7,8,9,9a-octahydro-1H-pyrido[1,2-a]pyrazine (Preparation 5), 2.48 g (21.2 mmol) of N-methylmorpholine-N-oxide, 5.0 g of 4 Å molecular sieves, 0.495 g (1.41 mmol) of tetrapropylammonium per-ruthenate, and 375 mL of methylene chloride was stirred at ambient temperature for 2 h. The reaction was quenched with saturated sodium thiosulfate and filtered through Celite. The filtrate was washed with brine, dried (magnesium sulfate), filtered and evaporated. Purification by flash silica gel chromatography with 95:5 chloroform:methanol gave 2.27 g (61%) of (7R,9aS)-7-formyl-2-(5-fluoropyrimidin-2-yl)-2,3,4,6,7,8,9,9a-octahydro-1H-pyrido[1,2-a]pyrazine.

A solution of 1.70 g (4.38 mmol) of benzyl triphenyl phosphonium chloride in 20 mL of dry THF was chilled to −78° C. and treated with 1.75 mL (4.38 mmol) of n-butyllithium (2.5 M in hexane). After 15 min, 1.05 g (3.98 mmol) of (7R,9aS)-7-formyl-2-(5-fluoropyrimidin-2-yl)-2,3,4,6,7,8,9,9a-octahydro-1H-pyrido[1,2-a]pyrazine in 20 mL of dry THF was added dropwise over 30 min, the cooling bath was removed and the solution allowed to warm slowly to ambient temperature overnight (16 h). The solution was concentrated in vacuo and the residue was partitioned between ethyl ether and water. The organic layer was dried (magnesium sulfate), filtered and evaporated. Purification by flash silica gel chromatography with petroleum ether:ethyl ether in ratios from 4:1 to 3:1 gave the following isomers of 7-(2-phenyl)ethenyl-2-(5-fluoropyrimidin-2-yl)-2,3,4,6,7,8,9,9a-octahydro-1H-pyrido[1,2-a]pyrazine: E-(7S,9aS), 0.19 g (Rf=0.75 with 3:1 hexane:ethyl acetate); Z-(7R,9aS), 0.16 g (Rf=0.47 with 3:1 hexane:ethyl acetate); E-(7R,9aS), 0.46 g (Rf=23 with 3:1 hexane:ethyl acetate).

A mixture of 0.15 g (0.44 mmol) of Z-(7R,9aS)-7-(2-phenyl)ethenyl-2-(5-fluoropyrimidin-2-yl)-2,3,4,6,7,8,9,9a-octahydro-1H-pyrido[1,2-a]pyrazine, 0.015 g of 10% palladium on carbon and 25 mL of ethanol was shaken under 40 psig of hydrogen gas in a Parr apparatus for 6 h. The mixture was filtered through Celite, and the filtrate concentrated to give 0.124 g (83%) of (7R,9aS)-7-(2-phenyl)ethyl-2-(5-fluoropyrimidin-2-yl)-2,3,4,6,7,8,9,9a-octahydro-1H-pyrido[1,2-a]pyrazine. mp (.HCl) 250–252° C. HRMS calcd for $C_{20}H_{26}FN_4O$ (MH+): 341.2142, found: 341.2126.

EXAMPLE 13

(7SR,9aSR)-7-Phenoxymethyl-2-(pyridin-2-yl)-2,3,4,6,7,8,9,9a-octahydro-1H-pyrido[1,2-a]pyrazine

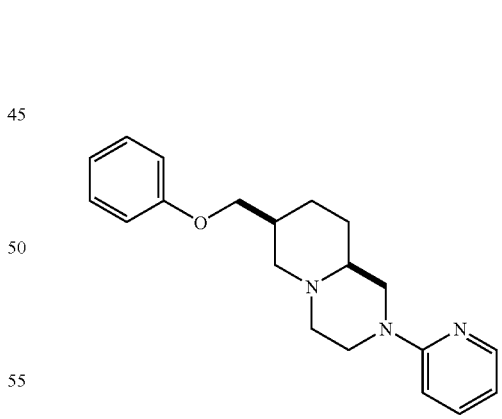

The title compound was prepared according to Example 8 from phenol and (7SR,9aSR)-hydroxymethyl-2,3,4,6,7,8,9,9a-octahydro-2-pyridin-2-yl-1H-pyrido[1,2-a]pyrazine (U.S. Pat. No. 5,122,525). $^{13}C$ NMR (base, CDCl$_3$): δ 24.8, 25.3, 33.8, 45.1, 50.7, 54.8, 56.6, 61.0, 68.8, 107.1, 113.1, 114.7, 120.5, 129.4, 137.4, 148.0, 159.3, 159.4. HRMS calcd for $C_{20}H_{25}N_3O$: 323.2000, found: 323.2003

EXAMPLE 14

(7RS,9aSR)-7-Phenoxymethyl-2-(pyridin-2-yl)-2,3,4,6,7,9,9a-octahydro-1H-pyrido[1,2-a]pyrazine

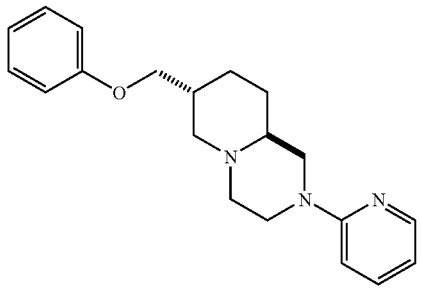

The title compound was prepared according to Example 9 from (7RS,9aSR)-hydroxymethyl-2-(pyridin-2-yl)-2,3,4,6,7,8,9,9a-octahydro-1H-pyrido[1,2-a]pyrazine (Preparation 11) and phenol. mp (.HCl) 238–241° C. $^{13}$C NMR (base, CDCl$_3$): δ 27.0, 29.2, 36.4, 45.2, 50.8, 54.8, 58.8, 60.7, 70.9, 107.0, 113.2, 114.5, 120.7, 113.2, 114.5, 120.7, 129.4, 137.5, 148.0, 159.0, 159.4. Anal. calcd for C$_{20}$H$_{25}$N$_3$O C, 74.26; H, 7.79; N, 12.99; found: C, 74.12; H, 7.84; N, 12.86.

EXAMPLE 15

(7RS,9aSR)-7-(4-Fluorophenoxy)methyl-2-(3,5-dichloropyridin-2-yl)-2,3,4,6,7,8,9,9a-octahydro-1H-pyrido[1,2-a]pyrazine

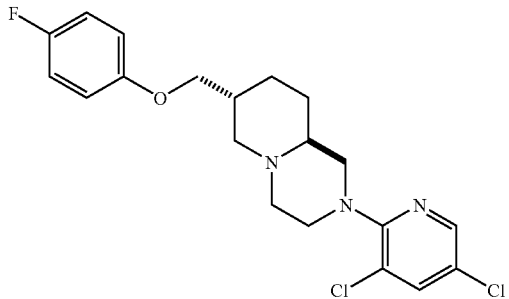

A mixture of 0.75 g (4.4 mmol) of (7RS,9aSR)-7-hydroxymethyl-2,3,4,6,7,8,9,9a-octahydro-1H-pyrido[1,2-a]pyrazine, 4.02 g (22.1 mmol) of 2,3,5-trichloropyridine, 1.12 g (10.6 mmol) of sodium carbonate and 30 mL of isoamylalcohol was refluxed for 72 h. The mixture was cooled to room temperature, filtered, and concentrated in vacuo. The residue was dissolved in ethyl acetate and washed with saturated sodium carbonate. The organic layer was dried (magnesium sulfate), filtered and evaporated, and the crude product was purified by flash chromatography on silica gel eluting with 95:5 chloroform:methanol to give 1.10 g (80%) of (7RS,9aSR)-7-hydroxymethyl-2-(3,5-dichloro-pyridin-2-yl)-2,3,4,6,7,8,9,9a-octahydro-1H-pyrido[1,2-a]pyrazine.

A solution of 0.50 g (1.58 mmol) of (7RS,9aSR)-7-hydroxymethyl-2-(3,5-dichloro-pyridin-2-yl)-2,3,4,6,7,8,9,9a-octahydro-1H-pyrido[1,2-a]pyrazine in 40 mL of THF with 0.266 g (2.32 mmol) of 4-fluorophenol, 0.498 g (1.90 mmol) of triphenylphosphine, and 0.30 mL (1.90 mmol) of diethyl azodicarboxylate was stirred at room temperature for 16 h. The mixture was diluted with ethyl acetate and treated with excess HCl(g) in ether. The solvent was evaporated and the residue washed repeatedly with 1:1 ethyl acetate:ether. The white powder was dissolved in chloroform, washed with 1M NaOH (2×), dried (magnesium sulfate), filtered and evaporated. The crude product was purified by flash silica gel chromatography with 50:50 ethyl acetate: hexane to give 0.566 g (87%) of title compound. mp (.HCl) 247–248° C. $^{13}$C NMR (base, CDCl$_3$): δ 27.1, 29.0, 36.4, 49.0, 54.4, 54.8, 58.6, 60.7, 71.7, 115.36, 115.47, 115.59, 115.89, 122.3, 124.0, 138.2, 155.1, 155.6, 156.6, 158.8. HRMS calc for C$_{20}$H$_{22}$Cl$_2$FN$_3$O: 409.1124, found: 409.1141.

EXAMPLE 16

7-(4-Fluorophenoxy)methyl-2-(substituted-pyridin-2-yl)-2,3,4,6,7,8,9,9a-octahydro-1H-pyrido[1,2-a]pyrazines

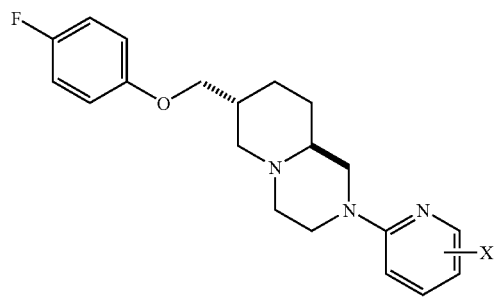

Compounds were prepared according to Example 15 from (7RS,9aSR)-7-hydroxymethyl-2,3,4,6,7,8,9,9a-octahydro-1H-pyrido[1,2-a]pyrazine (U.S. Pat. No. 5,326,874), using the appropriate 2-chloro or 2-bromo pyridine in the first step and 4-fluorophenol in the second step. Purification was generally accomplished by flash silica gel chromatography using mixtures of ethyl acetate and hexane or mixtures of chloroform and methanol as the eluting solvent. The stereochemical configuration, substituted pyridin-2-yl substitutent, melting point of the monohydrochloride salt and HRMS data are shown.

EXAMPLE 16a (7RS,9aSR), 2-(3-Cyanopyridin-2-yl); mp 194–195° C.; HRMS calcd for C$_{21}$H$_{23}$FN$_4$O: 366.1855; found: 366.1845.

EXAMPLE 16b (7RS,9aSR), 2-(4-Methylpyridin-2-yl); mp 264–266° C.; HRMS calcd for C$_{21}$H$_{26}$FN$_3$O: 355.2060, found: 355.2075.

EXAMPLE 16c (7RS,9aSR), 2-(5-Bromopyridin-2-yl); mp 214–215° C.; HRMS calcd for C$_{20}$H$_{23}$BrFN$_3$O: 419.1008, found: 419.1037.

EXAMPLE 16d (7RS,9aSR), 2-(3-Chloropyridin-2-yl); mp 174–175° C.; HRMS calcd for $C_{20}H_{23}ClFN_3O$: 375.1514, found: 375.1528.

EXAMPLE 17

(7RS,9aSR)-7-Phenoxymethyl-2-(5-chloropyridin-2-yl)-2,3,4,6,7,8,9,9a-octahydro-1H-pyrido[1,2-a]pyrazine

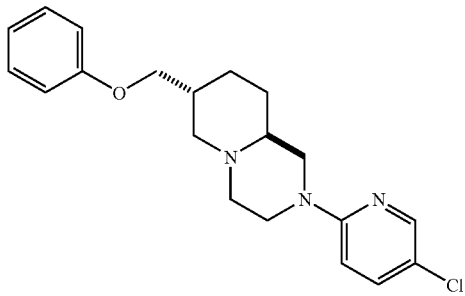

The title compound was prepared according to Example 15 using 2,5-dichloropyridine, (7RS,9aSR)-7-hydroxymethyl-2,3,4,6,7,8,9,9a-octahydro-1H-pyrido[1,2-a]pyrazine (U.S. Pat. No. 5,326,874), and phenol. mp (.HCl) 218–224° C. $^{13}$C NMR (base, CDCl$_3$): δ 27.0, 29.1, 36.4, 45.3, 50.9, 54.6, 58.8, 60.5, 70.9, 107.8, 114.5, 120.1, 120.7, 129.4, 137.1, 146.2, 157.6, 159.0. Anal. calcd for $C_{20}H_{24}ClN_3O$ C, 67.12; H, 6.76; N, 11.74; found: C, 67.22; H, 6.85; N, 11.49.

EXAMPLE 18

(7R,9aS)-7-(4-Fluorophenoxy)methyl-2-(pyridin-2-yl)-2,3,4,6,7,8,9,9a-octahydro-1H-pyrido[1,2-a]pyrazine

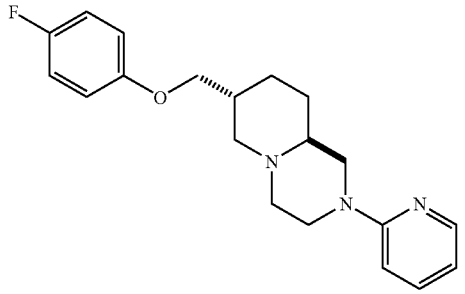

The title compound was synthesized according to Preparation 11 using 2-bromopyridine and (7R,9aS)-7-(4-fluorophenoxy)methyl-2,3,4, -6,7,8,9,9a-octahydro-1H-pyrido[1,2-a]pyrazine (Preparation 8). mp (.HCl) 261–263° C. HRMS calcd for $C_{20}H_{24}FN_3O$: 341.1903; found, 341.1928.

EXAMPLE 19

(7R,9aS)-7-(4-Fluorophenoxy)methyl-2-(5-chloropyridin-2-yl)-2,3,4,6,7,8,9,9a-octahydro-1H-pyrido[1,2-a]pyrazine

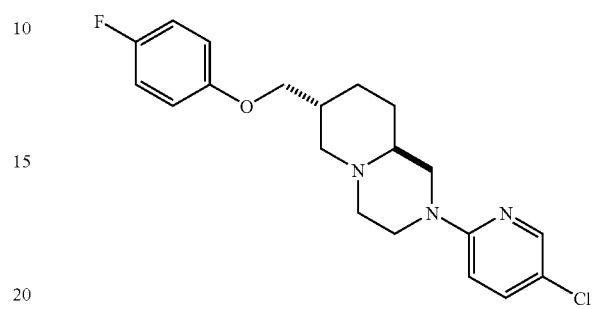

The title compound was prepared according to Preparation 11 using 2,5-dichloropyridine and (7R,9aS)-7-(4-fluorophenoxy)methyl-2,3,4,6,7,8,9,9a-octahydro-1H-pyrido[1,2-a]pyrazine (Preparation 8). mp (.HCl) 237–238° C. $^{13}$C NMR (base, CDCl$_3$): δ 27.0, 29.1, 36.4, 45.3, 50.9, 54.6, 58.7, 60.5, 71.6, 107.7, 115.36, 115.47, 115.60, 115.90, 120.1, 137.1, 146.3, 155.1, 155.6, 157.6, 158.8. HRMS calcd for $C_{20}H_{23}ClFN_3O$: 375.1514; found, 375.1544.

EXAMPLE 20

(7R,9aS)-7-(4-Fluorophenoxy)methyl-2-(6-chloropyridazin-3-yl)-2,3,4,6,7,8,9,9a-octahydro-1H-pyrido[1,2-a]pyrazine

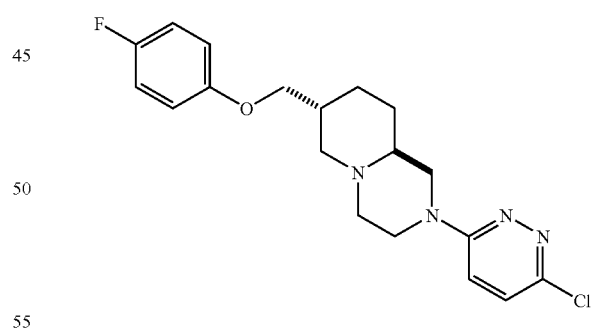

The title compound was prepared according to Preparation 3 with 3,6-dichloropyridazine and (7R,9aS)-7-(4-fluorophenoxy)methyl-2,3,4,6,7,8,9,9a-octahydro-1H-pyrido[1,2-a]pyrazine. mp (.HCl) 265–270° C. $^{13}$C NMR (base, CDCl$_3$): δ 26.8, 29.0, 36.4, 45.1, 50.4, 54.4, 58.6, 60.3, 71.5, 115.2, 115.3, 115.4, 115.6, 115.9, 128.7, 146.7, 155.0, 155.6, 158.76, 158.82. HRMS calcd for $C_{19}H_{22}ClFN_4O$: 376.1461; found: 376.1453.

EXAMPLE 21

(7S,9aR)-7-(4-Fluorophenoxy)methyl-2-(5-fluoropyrimidin-2-yl)-2,3,4,6,7,8,9,9a-octahydro-1H-pyrido[1,2-a]pyrazine

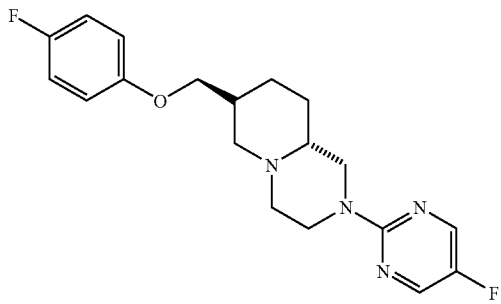

The title compound was prepared according to Preparation 3 with 2-chloro-5-fluoropyrimidine and (7S,9R)-7-(4-fluorophenoxy)methyl-2,3,4,6,7,8,9,9a-octahydro-1H-pyrido[1,2-a]pyrazine (Preparation 9). mp (.HCl) 251–252° C. $^{13}$C NMR (base, CDCl$_3$): δ 27.0, 29.0, 36.4, 44.3, 49.8, 54.8, 58.8, 60.7, 71.6, 115.35, 115.45, 115.59, 115.89, 145.0, 145.3, 149.9, 153.2, 155.1, 155.6, 158.7, 158.8. HRMS calcd for C$_{19}$H$_{22}$F$_2$N$_4$O: 360.1762; found: 360.1763.

EXAMPLE 22

(7R,9aR)-7-(4-Fluorophenoxy)methyl-2-(5-fluoropyrimidin-2-yl)-2,3,4,6,7,8,9,9a-octahydro-1H-pyrido[1,2-a]pyrazine

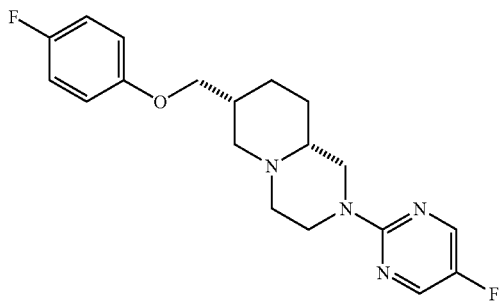

The title compound was prepared according to Preparation 3 with 2-chloro-5-fluoropyrimidine and (7R,9R)-7-(4-fluorophenoxy)methyl-2,3,4,6,7,8,9,9a-octahydro-1H-pyrido[1,2-a]pyrazine (Preparation 10). mp (.HCl) 232.5–324° C. $^{13}$C NMR (base, CDCl$_3$): δ 24.8, 25.1, 33.8, 44.3, 49.7, 54.8, 56.6, 61.0, 69.5, 115.48, 115.53, 115.59, 115.83, 145.0, 145.3, 149.9, 153.1, 155.4, 155.5, 158.69, 158.74. HRMS calcd for C$_{19}$H$_{22}$F$_2$N$_4$O: 360.1762; found: 360.1755.

EXAMPLE 23

(7RS,9aSR)-7-(4-Fluorophenoxy)methyl-2-(2-cyano-4-fluorophenyl)-2,3,4,6,7,8,9,9a-octahydro-1H-pyrido[1,2-a]pyrazine

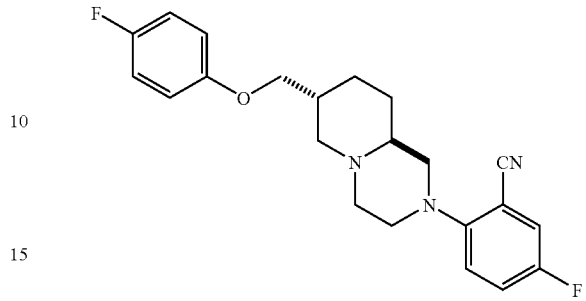

A mixture of 1.05 g (6.17 mmol) of (7RS,9aSR)-7-hydroxymethyl-2,3,4,6,7,8,9,9a-octahydro-1H-pyrido[1,2-a]pyrazine (U.S. Pat. No. 5,326,874) and 1.29 g (9.25 mmol) of 2,5-difluorobenzonitrile in 20 mL of DMSO was heated at 100° C. for 16 h. The mixture was cooled to room temperature, acidified with 1M HCl, washed with ether (3×), made basic with conc. ammonium hydroxide, and extracted with ethyl acetate (3×). The combined organic layers were washed with water (3×), dried (magnesium sulfate), filtered and evaporated. Purification by silica gel MPLC with 90:10 chloroform:methanol gave 0.51 g of (7RS,9aSR)-7-hydroxymethyl-2-(2-cyano4-fluorophenyl)-2,3,4,6,7,8,9,9a-octahydro-1H-pyrido[1,2-a]pyrazine.

A solution of 0.51 g (1.8 mmol) of (7RS,9aSR)-7-hydroxymethyl-2-(2-cyano-4-fluorophenyl)-2,3,4,6,7,8,9,9a-octahydro-1H-pyrido[1,2-a]pyrazine, 0.555 g (2.12 mmol) of triphenylphosphine, and 0.296 g (2.64 mmol) of 4-fluorophenol in 8 mL of dry THF was treated with 0.368 g (2.12 mmol) of diethyl azodicarboxylate and stirred at ambient temperature for 24 h. The mixture was diluted with ether, and 1M HCl was added until a gummy residue formed. The layers were separated and the aqueous layer was washed with ether (3×). The aqueous layer was combined with the gummy residue and dissolved in a mixture of ethyl acetate and 10% ammonium hydroxide, the layers were separated and the aqueous layer was extracted with more ethyl acetate (2×). The organic layers were evaporated, the residue dissolved in chloroform, washed with 1M NaOH (3×), dried (magnesium sulfate), filtered and evaporated. The product was dissolved in absolute ethanol, filtered and evaporated to give 0.21 g of the title compound. mp (.HCl) 235–240° C. HRMS calcd for C$_{22}$H$_{23}$F$_2$N$_3$O: 383.1809, found: 383.1796.

EXAMPLE 24

(7R,9aS)-7-(4-Fluorophenoxy)methyl-2-(2-amino-4-fluorophenyl)-2,3,4,6,7,8,9,9a-octahydro-1H-pyrido[1,2-a]pyrazine

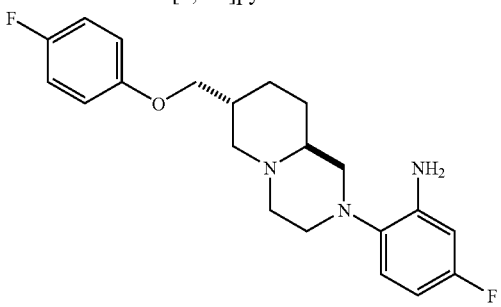

A solution of 4.38 g (25.8 mmol) of (7R,9aS)-7-hydroxymethyl-2,3,4,6,7,8,9,9a-octahydro-1H-pyrido[1,2-a]pyrazine (preparation 1), 4.19 mL (38.7 mmol) of 2,5-difluoronitrobenzene, and 5.46 g (51.5 mmol) of sodium carbonate in 25 mL of DMSO was heated at 95° C. for 16 h. The mixture was cooled to room temperature, acidified with 1M HCl, and washed with ethyl ether (3×). The aqueous layer was made basic with conc. ammonium hydroxide and extracted with ethyl acetate (3×). The combined organic layers were washed with water (3×), dried (magnesium sulfate), filtered and evaporated. Purification by flash silica gel chromatography with 90:10 chloroform:methanol gave 6.19 g (78%) of (7R,9aS)-7-hydroxymethyl-2-(4-fluoro-2-nitrophenyl)-2,3,4,6,7,8,9,9a-octahydro-1H-pyrido[1,2-a]pyrazine.

A solution of 3.0 g (9.7 mmol) of (7R,9aS)-7-hydroxymethyl-2-(4-fluoro-2-nitrophenyl)-2,3,4,6,7,8,9,9a-octahydro-1H-pyrido[1,2-a]pyrazine in 50 mL of methanol and 50 mL of THF was treated with 0.30 g of 10% Pd/C and treated with 30 psi of hydrogen in a Parr apparatus for 1.5 h. The catalyst was removed by filtration and the red solution concentrated to give 2.65 g (98%) of (7R,9aS)-7-hydroxymethyl-2-(2-amino-4-fluorophenyl)-2,3,4,6,7,8,9,9a-octahydro-1H-pyrido[1,2-a]pyrazine.

A solution of 4.12 g (14.8 mmol) of (7R,9aS)-7-hydroxymethyl-2-(2-amino-4-fluoro-phenyl)-2,3,4,6,7,8,9,9a-octahydro-1H-pyrido[1,2-a]pyrazine, 2.48 g (22.2 mmol) of 4-fluorophenol and 4.65 g (17.7 mmol) of triphenylphosphine in 225 mL of THF was treated with 2.79 mL (17.7 mmol) of diethyl azodicarboxylate and stirred at room temperature for 4 days. The solvent was evaporated, the residue dissolved in 1:1 ethyl acetate:ethyl ether and the solution treated with HCl(g) in ether until precipitation ceased. The mixture was filtered and the solid washed repeatedly with ethyl acetate. The solid was dissolved in a mixture of chloroform and 1M sodium hydroxide, the layers separated, and the organic phase was dried (magnesium sulfate), filtered and evaporated. Purification by flash silica gel chromatography with 60:40 ethyl acetate:hexane gave 1.69 g (30%) of the title compound. mp (.HCl) 144–149° C. HRMS calcd for $C_{21}H_{25}F_2N_3O$: 373.1966, found: 373.1958.

EXAMPLE 25

(7RS,9aSR)-7-(4-Fluorophenoxy)methyl-2-(4-fluorophenyl)-2,3,4,6,7,8,9,9a-octahydro-1H-pyrido[1,2-a]pyrazine

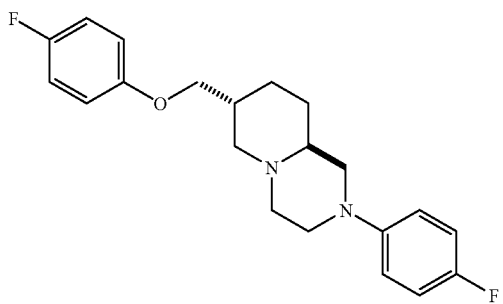

A solution of 1.53 g (4.10 mmol) of (7R,9aS)-7-hydroxymethyl-2-(2-amino-4-fluoro-phenyl)-2,3,4,6,7,8,9,9a-octahydro-1H-pyrido[1,2-a]-pyrazine (Example 24) in 160 mL of THF was added to a solution of 1.21 mL (9.02 mmol) of 97% isoamyl nitrite in 100 mL of THF over a 2 h period. After the addition was complete, the solution was heated at reflux for 4 days. The solvent was evaporated, the residue was dissolved in ethyl acetate and washed with 1M sodium hydroxide (3×). The organic phase was dried (magnesium sulfate), filtered and evaporated. Purification by flash silica gel chromatography with 50:50 ethyl acetate:hexane gave 0.75 g (52%) of a yellow solid. mp (.HCl) 221–223° C. HRMS calcd for $C_{21}H_{24}F_2N_2O$: 358.1857, found 358.1875.

EXAMPLE 26

(7R,9aS)-7-Phenoxymethyl-2-phenyl-2,3,4,6,7,8,9,9a-octahydro-1H-pyrido[1,2-a]pyrazine

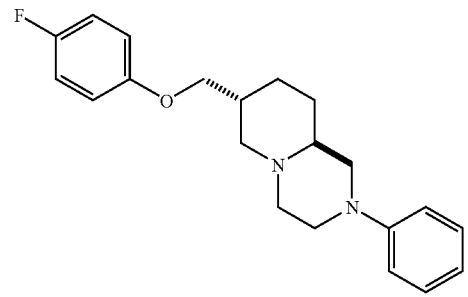

A mixture of 0.500 g (1.89 mmol) of (7R,9aS)-7-(4-fluorophenoxy)methyl-2,3,4,6,7,8,9,9a-octahydro-1H-pyrido[1,2-a]pyrazine (Preparation 8), 0.400 g (2.84 mmol) of 4-fluoronitrobenzene and 0.401 g (3.78 mmol) of sodium carbonate in 15 mL of DMSO was heated at 95° C. for 16 h. The mixture was cooled to room temperature, acidified with 1M HCl, washed with ethyl ether (3×), basified with conc. ammonium hydroxide and extracted with ethyl acetate (3×). The combined organic layers were washed with water and brine, dried (magnesium sulfate), filtered and evaporated to give 0.614 g of (7R,9aS)-7-(4-fluorophenoxy)-methyl-2-(4-nitrophenyl)-2,3,4,6,7,8,9,9a-octahydro-1H-pyrido[1,2-a]pyrazine.

A mixture of 0.600 g (1.56 mmol) of (7R,9aS)-7-(4-fluorophenoxy)methyl-2-(4-nitrophenyl)-2,3,4,6,7,8,9,9a-octahydro-1H-pyrido[1,2-a]pyrazine and 90 mg of 10% Pd/C in 25 mL of THF was placed in a Parr hydrogenator at 30 psi for 4 h. The catalyst was removed by filtration through Celite and the filtrate was evaporated to give 0.45 g (82%) of (7R,9aS)-7-(4-fluorophenoxy)methyl-2-(4-aminophenyl)-2,3,4,6,7,8,9,9a-octahydro-1H-pyrido[1,2-a]pyrazine.

A solution of 0.400 g (1.13 mmol) of (7R,9aS)-7-(4-fluorophenoxy)methyl-2-(4-aminophenyl)-2,3,4,6,7,8,9,9a-octahydro-1H-pyrido[1,2-a]pyrazine in 20 mL of THF was added dropwise to a solution of 0.33 mL (2.48 mmol) of isoamyl nitrite in 15 mL of THF. After the addition was complete, the solution was refluxed for 24 h. The solvent was evaporated, the residue dissolved in ethyl acetate, washed with 1M sodium hydroxide (3×), washed with brine (1×), dried (magnesium sulfate), filtered and evaporated. Purification by flash silica gel chromatography with ethyl acetate gave 0.060 g (16%) of the title compound. mp (.HCl) 247–252° C. HRMS calcd for $C_{21}H_{25}FN_2O$: 340.1951, found: 340.1989.

EXAMPLE 27

(7RS,9aSR)-7-(4-Fluorophenoxy)methyl-2-(6-methoxypyridin-2-yl)-2,3,4,6,7,8,9,9a octahydro-1H-pyrido[1,2-a]pyrazine

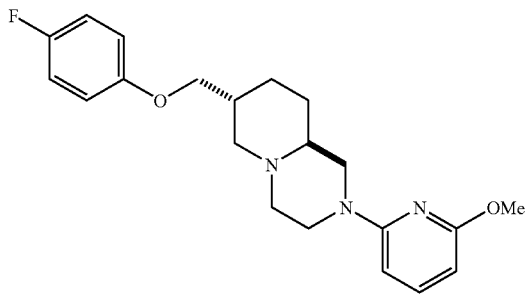

According to the procedure reported by Wynberg (*J. Org. Chem.* 1993, 58, 5101), a solution 0.50 g (2.9 mmol) of racemic (7RS,9aSR)-7-hydroxymethyl-2,3,4,6,7,8,9,9a-octahydro-1H-pyrido[1,2-a]pyrazine in 10 mL of dry THF at 0° C. was treated with 2.59 mL (6.5 mmol) of n-butyl lithium (2.5 M in hexane). The mixture was kept at 0° C. for 30 min and at room temperature for 1 h, and 0.39 mL (2.94 mmol) of 2,6-dimethoxypyridine was added and the solution refluxed for 16 h. After cooling to room temperature, the mixture was poured into 1 M HCl and washed with toluene (3×). The aqueous layer was basified with 1 M NaOH and extracted with toluene (1×) and ethyl acetate (1×). The combined organic layers were dried (magnesium sulfate), filtered, and evaporated to give a yellow oil. Purification by flash silica gel chromatography with 9:1 chloroform:methanol gave 0.304 g (37%) of (7RS,9aSR)-7-hydroxymethyl-2-(6-methoxypyridin-2-yl)-2,3,4,6,7,8,9,9a-octahydro-1H-pyrido[1,2-a]pyrazine.

A solution of 0.30 g (1.1 mmol) of (7RS,9aSR)-7-hydroxymethyl-2-(6-methoxypyridin-2-yl)-2,3,4,6,7,8,9,9a-octahydro-1H-pyrido[1,2-a]pyrazine, 0.182 g (1.62 mmol) of 4-fluorophenol, and 0.340 g (1.30 mmol) of triphenylphosphine, and 0.205 g (1.30 mmol) of diethylazodicarboxylate in 20 mL of THF was stirred at room temperature for 16 h. The solvent was evaporated, the residue dissolved in ether and extracted with 1M HCl (2×). The combined aqueous layers were basified with conc. ammonium hydroxide and extracted with ethyl acetate (3×). The combined organic layers were dried (magnesium sulfate), filtered and evaporated. Purification by flash silica gel chromatography with 50:50 ethyl acetate:hexane gave 0.300 g (75%) of yellow crystals. mp (.HCl) 228–230° C. HRMS calcd for $C_{21}H_{26}FN_3O_2$: 371.2009, found: 371.2001.

EXAMPLE 28

(7RS,9aSR)-7-(4-Fluorophenoxy)methyl-2,3,4,6,7,8,9,9a-octahydro-2-(5-fluoropyridin-2-yl)-1H-pyrido[1,2-a]pyrazine

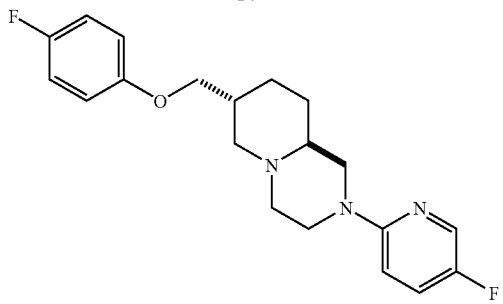

According to the procedure reported by Schwartz (*J. Am. Chem. Soc.* 1986, 108, 2445), a solution of 0.300 g (0.714 mmol) of (7RS,9aSR)-7-(4-fluorophenoxy)methyl-(5-bromopyridin-2-yl)-2,3,4,6,7,8,9,9a-octahydro-1H-pyrido[1,2-a]pyrazine (Example 16) in 6.5 mL of THF:hexane:ethyl ether (4:1:1) under nitrogen was cooled to –100° C. n-Butyl lithium (0.57 mL, 2.5 M in hexane) was added dropwise and the mixture stirred for 15 min. N-Fluorodibenzenesulfonamide (0.34 g, 1.07 mmol) in ethyl ether was added, the solution stirred for 20 min, and then allowed to warm to room temperature over 20 h. Water was added and the mixutre extracted with ethyl acetate (3×), dried (magnesium sulfate), filtered and evaporated. Purification by flash silica gel chromatography with 50:50 ethyl acetate:hexane gave 0.038 g (15%) of the title compound. mp (.HCl) 214–215° C. HRMS calcd for $C_{20}H_{23}F_2N_3O$: 359.1809, found: 359.1795.

EXAMPLE 29

(7RS,9aSR)-7-Phenoxymethyl-2-(2-chloropyrimidin-4-yl)-2,3,4,6,7,8,9,9a-octahydro-1H-pyrido[1,2-a]pyrazine

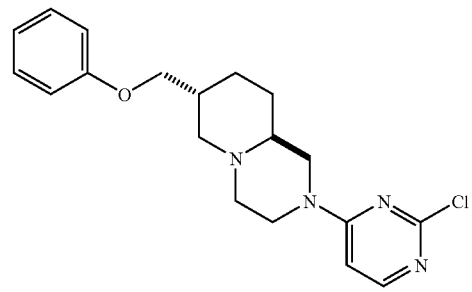

A mixture of (7RS,9aSR)-7-hydroxymethyl-2,3,4,6,7,8,9,9a-octahydro-1H-pyrido[1,2-a]pyrazine (U.S. Pat. No. 5,326,874) and 2,4-dichloropyrimidine were combined according to Preparation 3. The product from this reaction was coupled with phenol according to Example 1 to give the title compound. mp (.HCl) 227–233° C. (dec). HRMS calcd for $C_{19}H_{23}ClN_4O$: 358.1560, found: 358.1560.

EXAMPLE 30

(7RS,9aSR)-7-Phenoxymethyl-2-(pyrazin-2-yl)-2,3,4,6,7,8,9,9a-octahydro-1H-pyrido[1,2-a]pyrazine

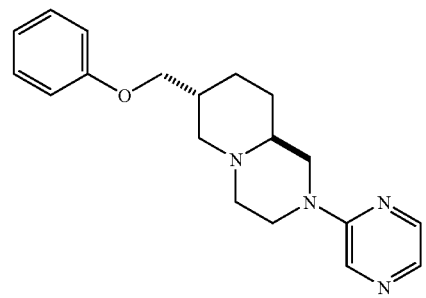

A mixture of (7RS,9aSR)-7-hydroxymethyl-2,3,4,6,7,8,9,9a-octahydro-1H-pyrido[1,2-a]pyrazine (U.S. Pat. No.

5,326,874) and 2-chloropyrazine were combined according to Preparation 3. The product from this reaction was coupled with phenol according to Example 1 to give the title compound. mp (.HCl) 217–219° C. HRMS calcd for $C_{19}H_{24}N_4O$: 324.1945, found: 324.1981.

EXAMPLE 31

(7RS,9aSR)-7-Phenoxymethyl-2-(6-chloropyrazin-2-yl)-2,3,4,6,7,8,9,9a-octahydro-1H-pyrido[1,2-a]pyrazine

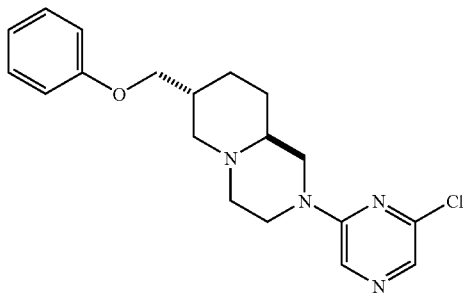

A mixture of (7RS,9aSR)-7-hydroxymethyl-2,3,4,6,7,8,9,9a-octahydro-1H-pyrido[1,2-a]pyrazine (U.S. Pat. No. 5,326,874) and 2,6-dichloropyrazine were combined according to Preparation 3. The product from this reaction was coupled with phenol according to Example 1 to give the title compound. mp (.HCl) 247° C. (dec). HRMS calc for $C_{19}H_{23}ClN_4O$: 358.1560, found: 358.160

EXAMPLE 32

(7RS, 9aSR)-7-(4-Fluorophenoxy)methyl-2-(6-chloropyrazin-3-yl)-2,3,4,6,7,8,9,9a-octahydro-1H-pyrido[1,2-a]pyrazine

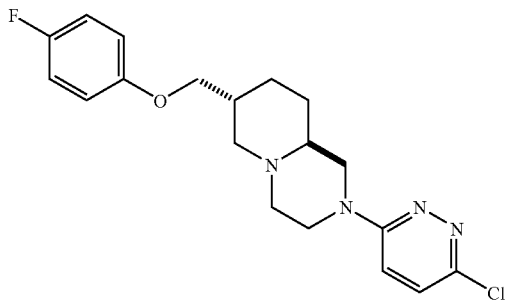

A mixture of (7RS,9aSR)-7-hydroxymethyl-2,3,4,6,7,8,9, 9a-octahydro-1H-pyrido[1,2-a]pyrazine (U.S. Pat. No. 5,326,874) and 3,6-di-chloropyridazine were combined according to Preparation 3. The product from this reaction was coupled with 4-fluorophenol according to Example 1 to give the title compound. mp (.HCl) 255° C. (dec) HRMS calc for $C_{19}H_{22}ClFN_4O$: 376.1461, found: 376.1458.

EXAMPLE 33

(7RS,9aSR)-7-Phenoxymethyl-2-(6-chloropyridazin-3-yl)-2,3,4,6,7,8,9,9a-octahydro-1H-pyrido[1,2-a]pyrazine

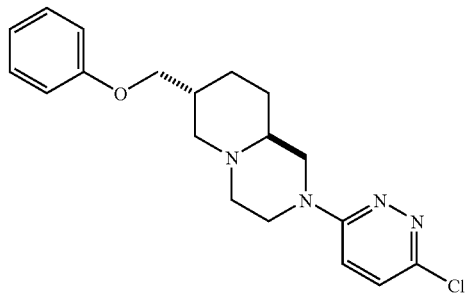

A mixture of (7RS,9aSR)-7-hydroxymethyl-2,3,4,6,7,8,9, 9a-octahydro-1H-pyrido[1,2-a]pyrazine (U.S. Pat. No. 5,326,874) and 3,6-dichlornpyridazine were combined according to Preparation 3. The product from this reaction was coupled with phenol according to Example 1 to give the title compound. mp (.HCl)>265° C. (dec). HRMS calcd for $C_{19}H_{23}ClN_4O$: 358.1555, found: 358.1550.

EXAMPLE 34

(7RS,9aSR)-7-Phenoxymethyl-2-(pyrimidin-4-yl)-2,3,4,6,7,8,9,9a-octahydro-1H-pyrido[1,2-a]pyrazine

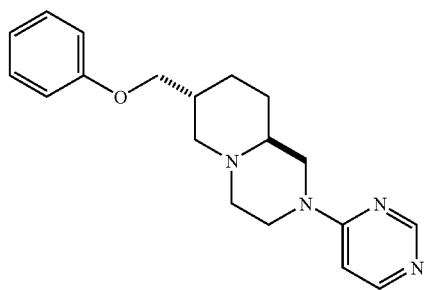

A mixture of 0.110 g (0.307 mmol) of (7RS,9aSR)-7-phenoxymethyl-2-(2-chloropyrimidin4-yl)-2,3,4,6,7,8,9,9a-octahydro-1H-pyrido[1,2-a]pyrazine (Example 29), 20 mg of 10% Pd/C, and several drops of conc. hydrochloric acid in 30 mL of ethanol were shaken under 50 psi of hydrogen gas at room temperature for 6 h. The mixture was filtered through Celite and the filtrate was evaporated. The residue was basified with conc. ammonium hydroxide, extracted with chloroform, dried (magnesium sulfate), filtered and evaporated. Purification by flash silica gel chromatography with a solvent gradient from 100% chloroform to 95:5 chloroform:methanol gave 0.020 g (20%) of the title compound. mp (.HCl) >265° C. (dec). HRMS calc for $C_{19}H_{24}N_4O$: 324.1945, found: 324.1970.

EXAMPLE 35

(7RS,9aSR)-7-(4-Fluorophenoxy)methyl-2-(pyridazin-3-yl)-2,3,4,6,7,8,9,9a-octahydro-1H-pyrido[1,2-a]pyrazine

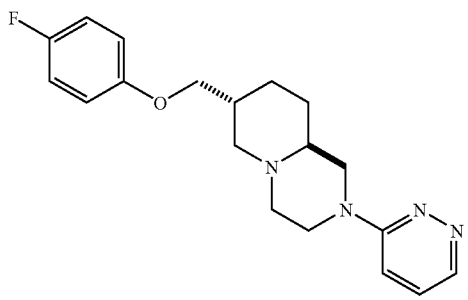

A mixture of 0.150 g (0.363 mmol) of (7RS,9aSR)-7-(4-fluorophenoxy)methyl-2-(6-chloropyridazin-3-yl)-2,3,4,6,7,8,9,9a-octahydro-1H-pyrido[1,2-a]pyrazine (Example 32). 0.10 mL (0.72 mmol) of triethylamine, and 20 mg of 10% Pd/C in 10 mL of ethanol were shaken under 50 psi of hydrogen for 18 h. The mixture was filtered through Celite and the filtrate was evaporated. The residue was dissolved in chloroform, washed with water, dried (magenesium sulfate), filtered and evaporated. mp (.HCl) 246–250° C. HRMS calcd for $C_{19}H_{23}FN_4O$: 342.1851, found: 342.1826.

EXAMPLE 36

(7R,9aS)-7-(3,5-Difluorophenoxy)methyl-2-(6-chloropyridazin-3-yl)-2,3,4,6,7,8,9,9a-octahydro-1H-pyrido[1,2-a]pyrazine

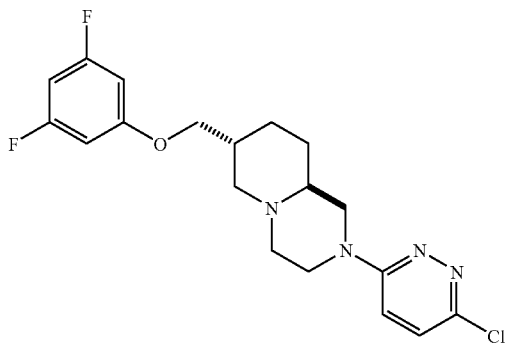

A mixture of (7R,9aS)—N—BOC-7-hydroxymethyl-2,3,4,6,7,8,9,9a-octahydro-1H-pyrido[1,2-a]pyrazine (WO 93/25552) and 3,5-difluorophenol were coupled followed by N—BOC deprotection according to Preparation 9. The product from this reaction was coupled with 3,6-dichloropyridazine according to Preparation 3 to give the title compound. mp (.HCl) 254–259° C. $^{13}$C NMR (base, CDCl$_3$): δ 26.7, 28.9, 36.1, 45.1, 50.4, 54.3, 58.4, 60.3, 71.4, 96.3, 95.0, 98.4, 115.2, 128.8, 146.8, 158.8.

EXAMPLE 37

(7R,9aS)-7-Phenoxymethyl-2-(5-chloropyridin-2-yl)-2,3,4,6,7,8,9,9a-octahydro-1H-pyrido[1,2-a]pyrazine

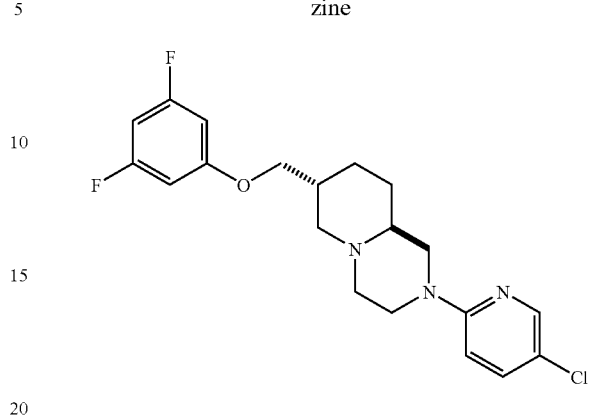

A mixture of (7R,9aS)—N—BOC-7-hydroxymethyl-2,3,4,6,7,8,9,9a-octahydro-1H-pyrido[1,2-a]pyrazine (WO 93/25552) and 3,5-difluorophenol were coupled followed by N—BOC deprotection according to Preparation 9. The product from this reaction was coupled 260–261° C. HRMS calcd for $C_{20}H_{22}ClF_2N_3O$: 393.1419, found: 393.1410.

EXAMPLE 38

3-[(7R,9aS)-2-Heteroaryl-2,3,4,6,7,8,9,9a-octahydro-1H-pyrido[1,2-a]pyrazin-7-ylmethyl]-3H-benzoxazol-2-ones

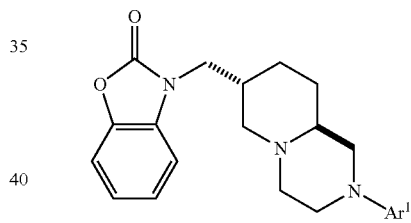

Compounds of the above formula were synthesized from 3-[(7R,9aS)-2,3,4,6,7,8,9,9a-octahydro-1H-pyrido[1,2-a]-pyrazin-7-ylmethyl]-3H-benzooxazol-2-one (Preparation 12) and the appropriate heteroaryl chloride according to Preparation 5. Purification was generally accomplished by flash silica gel chromatography using mixtures of ethyl acetate and hexane or mixtures of chloroform and methanol as the eluting solvent. The 2-substituent, melting point of the monohydrochloride and high resolution mass spectral data are shown.

EXAMPLE 38a 2-(Pyrimidin-2-yl); mp 165–167° C.; HRMS calcd for $C_{20}H_{23}N_5O_2$: 365.1852, found: 365.1850.

EXAMPLE 38b 2-(5-Fluoropyrimidin-2-yl); mp 170–171° C.; HRMS calcd for $C_{20}H_{22}FN_5O_2$: 383.1758, found: 383.1809.

EXAMPLE 38c 2-(6-Chloropyridazin-3-yl); mp 176° C. (dec); HRMS calcd for $C_{20}H_{22}ClN_5O_2$: 399.1457, found: 399.1519.

EXAMPLE 39

3-[(7R,9aS)-2-(5-Chloropyridin-2-yl)-2,3,4,6,7,8,9,9a-octahydro-1H-pyrido[1,2-a]-pyrazin-7-ylmethyl]-3H-benzoxazol-2-one

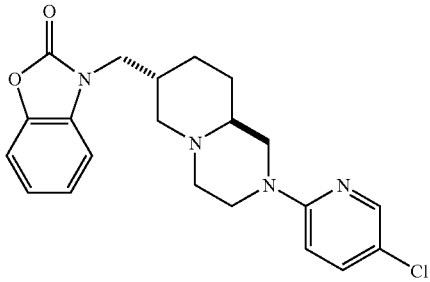

The title compound was synthesized according to Preparation 11 from 3-[(7R,9aS)-2,3,4,6,7,8,9,9a-octahydro-1H-pyrido[1,2-a]-pyrazin-7-ylmethyl]-3H-benzoxazol-2-one (Preparation 12) and 2,5-dichloropyridine. mp (.HCl) 247–248° C. HRMS calcd for $C_{21}H_{23}ClN_4O_2$: 398.1510, found: 398.1484.

EXAMPLE 40

(7RS,9aSR)-7-(5-Fluoroindol-1-ylmethyl)-2-(pyrimidin-2-yl)-2,3,4,6,7,8,9,9a-octahydro-1H-pyrido[1,2-a]pyrazine

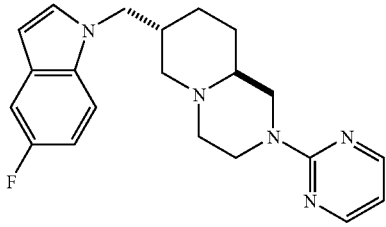

The title compound was synthesized according to Example 9 from (7RS,9aSR)-7-hydroxymethyl-2-(pyrimidin-2-yl)-2,3,4,6,7,8,9,9a-octahydro-1H-pyrido[1,2-a]pyrazine (Preparation 3) and 5-fluoroindole. mp (.HCl) 70–72° C. HRMS calcd for $C_{21}H_{25}FN_5$(MH+): 366.2094, found: 366.2104.

EXAMPLE 41

(7RS,9aSR)-7-(4-Fluorophenylsulfanyl)methyl-2-pyrimidin-2-yl)-2,3,4,6,7,8,9,9a-octahydro-1H-pyrido[1,2-a]pyrazine

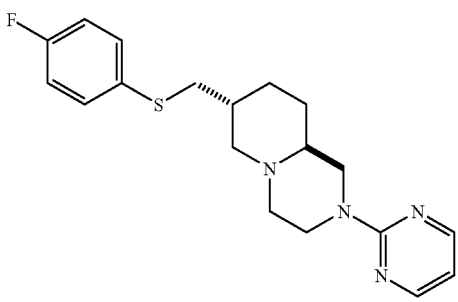

The title compound was prepared according to Example 1 from (7RS,9aSR)-7-hydroxymethyl-2-(2-pyrimidin-2-yl)-2, 3,4,6,7,8,9,9a-octahydro-1H-pyrido[1,2-a]pyrazine (Preparation 3) and 4-fluorothiophenol. mp (.HCl) 99–101° C. HRMS calcd for $C_{19}H_{23}FN_4S$: 358.1627, found: 358.1683.

EXAMPLE 42

(7RS,9aSR)-7-(4-Fluorophenylsulfonyl)methyl-2-(pyrimidin-2-yl)-2,3,4,6,7,8,9,9a-octahydro-1H-pyrido[1,2-a]pyrazine

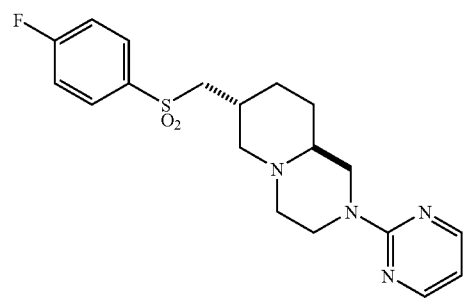

A solution of 0.50 g (1.40 mmol) of (7RS,9aSR)-7-(4-fluorophenylsulfanyl)methyl-2-(pyrimidin-2-yl)-2,3,4,6,7,8,9,9a-octahydro-1H-pyrido[1,2-a]pyrazine (Example 41) and 1.13 g (5.59 mmol) of 3-chloroperbenzoic acid in 30 mL of chloroform was stirred at room temperature for 20 h. The solution was partitioned with 1M sodium hydroxide, the layers were separated, the organic phase was dried (magnesium sulfate), filtered and evaporated. Purification by flash silica gel chromatography with 67:33 chloroform:methanol gave 0.18 g (33%) of the title compound. mp (.HCl) 155–157° C. HRMS calcd for $C_{19}H_{23}FN_4O_2S$: 390.1526, found: 390.1483.

EXAMPLE 43

(7R,9aS)-7-(5-Fluoroindol-1-yl)methyl-2-(5-fluoropyrimidin-2-yl)-2,3,4,6,7,8,9,9a-octahydro-1H-pyrido[1,2-a]pyrazine

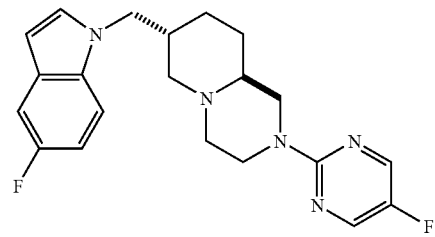

A solution of 6.0 g (22 mmol) of (7R,9aS)-2-BOC-7-hydroxymethyl-2,3,4,6,7,8,9,9a-octahydro-1H-pyrido[1,2-a]pyrazine (WO 93/25552) and 3.41 mL (24.4 mmol) of triethylamine in 225 mL of dry methylene chloride was chilled to 0° C., and treated with 1.80 mL (23.3 mmol) of methansulfonyl chloride in 75 mL of methylene chloride. After stirring 1 h, water was added and the pH adjusted to 12 with 15% sodium hydroxide. The layers were separated and the aqueous phase extracted with methylene chloride. The combined organic phase was dried (magnesium sulfate), filtered and evaporated to give 7.73 g (100%) of (7R,9aS)-

2-BOC-7-(methanesulfonyloxy)methyl-2,3,4,6,7,8,9,9a-octahydro-1H-pyrido[1,2-a]pyrazine.

A solution of 8.41 g (62 mmol) of 5-fluoroindole in 250 mL of DMF was treated with 2.46 g (62 mmol) of sodium hydride (60% oil dispersion) and the mixture stirred at 50° C. for 1.5 h. Heating was stopped temporarily, 7.73 g (22.2 mmol) of (7R,9aS)-2-BOC-7-(methanesulfonyloxy)methyl-2,3,4,6,7,8,9,9a-octahydro-1H-pyrido[1,2-a]pyrazine in 250 mL of DMF was added and the mixture stirred at 100° C. for 2 h. The mixture was cooled to room temperature, diluted with water, acidified to pH 2 with 6M hydrochloric acid, and washed with ethyl acetate. The aqueous phase was basified to pH 12 with conc. ammonium hydroxide and extracted with ethyl acetate (3×). The combined organic phase was dried (magnesium sulfate), filtered and evaporated. Purification by flash silica gel chromatography with ethyl acetate gave 3.09 g (36%) of (7R,9aS)-2-BOC-7-(5-flubroindol-1-yl)methyl-2,3,4,6,7,8,9,9a-octahydro-1H-pyrido[1,2-a]pyrazine.

A solution of 3.0 g (7.75 mmol) of (7R,9aS)-2-BOC-7-(5-fluoroindol-1-yl)methyl-2,3,4,6,7,8,9,9a-octahydro-1H-pyrido[1,2-a]pyrazine in 200 mL of 70:30 trifluoroacetic acid:water was stirred at room temperature for 1 h. The mixture was concentrated in vacuo, basified with 15% sodium hydroxide and extracted with ethyl acetate (2×). The combined organics were dried (magnesium sulfate), filtered and evaporated to give 2.0 g (90%) of (7R,9aS)-7-(5-fluoroindol-1-yl)methyl-2,3,4,6,7,8,9,9a-octahydro-1H-pyrido[1,2-a]pyrazine.

A mixture of 2.20 g (7.67 mmol) of (7R,9aS)-7-(5-fluoroindol-1-yl)methyl-2,3,4,6,7,8,9,9a-octahydro-1H-pyrido[1,2-a]pyrazine, 1.02 g (7.67 mmol) of 2-chloro-5-fluoropyrimidine and 1.95 g (18.4 mmol) of sodium carbonate in 100 mL of water was stirred at 95° C. for 72 h. The mixture was cooled to room temperature, extracted with chloroform (3×), the combined organic phase was washed with brine, dried (magnesium sulfate), filtered and evaporated. Purification by flash silica gel chromatography with 50:50 ethyl acetate:hexane gave 1.17 g (40%) of the title compound. mp (.HCl) 180–182° C. HRMS calc for HRMS calcd for $C_{21}H_{23}F_2N_5$: 383.1922, found: 383.1924.

EXAMPLE 44

1-[(7R,9aS)-2-(Pyrimidin-2-yl)-2,3,4,6,7,8,9,9a-octahydro-1H-pyrido[1,2-a]pyrazin-7-ylmethyl]-1,3-dihydro-indol-2-one

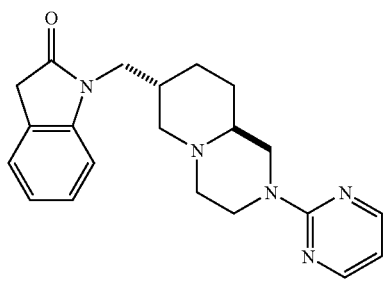

A solution of 6.0 g (22 mmol) of (7R,9aS)-2-BOC-7-hydroxymethyl-2,3,4,6,7,8,9,9a-octahydro-1H-pyrido[1,2-a]pyrazine (WO 93/25552) and 3.41 mL (24.4 mmol) of triethylamine in 225 mL of dry methylene chloride was chilled to 0° C., and treated with 1.80 mL (23.3 mmol) of methansulfonyl chloride in 75 mL of methylene chloride. After stirring 1 h, water was added and the pH adjusted to 12 with 15% sodium hydroxide. The layers were separated and the aqueous phase extracted with methylene chloride. The combined organic phase was dried (magnesium sulfate), filtered and evaporated to give 7.73 g (100%) of (7R,9aS)-2-BOC-7-(methanesulfonyloxy)methyl-2,3,4,6,7,8,9,9a-octahydro-1H-pyrido[1,2-a]pyrazine.

A solution of 2.75 g (10.7 mmol) of oxindole in 85 mL of DMF was treated with 0.82 g (21 mmol) of sodium hydride (60% oil dispersion) and the mixture stirred at 50° C. for 1.5 h. Heating was stopped temporarily, 2.56 g (7.38 mmol) of (7R,9aS)-2-BOC-7-(methanesulfonyloxy)methyl-2,3,4,6,7,8,9,9a-octahydro-1H-pyrido[1,2-a]pyrazine in 85 mL of DMF was added, and the mixture stirred at 100° C. for 2 h. The mixture was cooled to room temperature, diluted with water, acidified to pH 2 with 6M hydrochloric acid, and washed with ethyl acetate. The aqueous phase was basified to pH 12 with conc. ammonium hydroxide and extracted with ethyl acetate (3×). The combined organic phase was dried (magnesium sulfate), filtered and evaporated. Purification by flash silica gel chromatography with ethyl acetate gave 0.677 g (24%) of 1-[(7R,9aS)-2-BOC-2,3,4,6,7,8,9,9a-octahydro-1H-pyrido[1,2-a]pyrazin-7-ylmethyl)]-1,3-dihydro-indol-2-one.

A solution of 0.53 g (1.38 mmol) of 1-[(7R,9aS)-2-BOC-2,3,4,6,7,8,9,9a-octahydro-1H-pyrido[1,2-a]pyrazin-7-ylmethyl]-1,3-dihydro-indol-2-one in 10 mL of chloroform was treated with excess HCl(g) in ethyl ether and stirred at room temperature for 1 h. The solvent was evaporated to give 0.49 g (100%) of 1-[(7R,9aS)-2,3,4,6,7,8,9,9a-octahydro-1H-pyrido[1,2-a]pyrazin-7-ylmethyl]-1,3-dihydro-indol-2-one dihydrochloride.

A mixture of 0.49 g (1.38 mmol) of 1-[(7R,9aS-2,3,4,6,7,8,9,9a-octahydro-1H-pyrido[1,2-a]pyrazin-7-ylmethyl]-1,3-dihydro-indol-2-one dihydrochloride, 0.157 g (1.37 mmol) of 2-chloropyrimidine and 0.64 g (6.02 mmol) of sodium carbonate in 20 mL of water was stirred at 95° C. for 16 h. The mixture was cooled to room temperature, extracted with chloroform (3×), the combined organic phase was washed with brine, dried (magnesium sulfate), filtered and evaporated. Purification by flash silica gel chromatography with 95:5 ethyl acetate:methanol gave 0.181 g (30%) of the title compound. mp (.HCl) 174–176° C. HRMS calcd for $C_{21}H_{25}N_5O$: 363.2059, found: 363.2032.

EXAMPLE 45

(7RS,9aSR)-7-Phenoxy-2-(pyrimidin-2-yl)-2,3,4,6,7,8,9,9a-octahydro-1H-pyrido[1,2-a]pyrazine

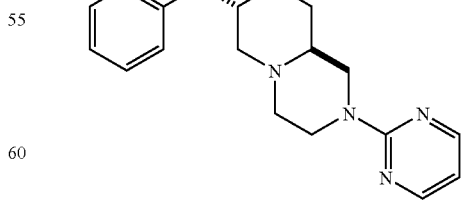

A solution of 0.600 g (3.03 mmol) of (9aSR)-7-(ethylenedioxy)-2,3,4,6,7,8,9,9a-octahydro-1H-pyrido[1,2-a]pyrazine (Compernolle, F.; Slaeh, M. A.; Toppet, S.; Hoornaert, G. J. Org. Chem., 1991, 56, 5192), 0.35 g (3.0 mmol)

of 2-chloropyrimidine and 0.77 g (7.3 mmol) of sodium carbonate in 6 mL of water was refluxed for 21 h. The mixture was cooled to room temperature, extracted with methylene chloride (3×), the combined organic phase was washed with water and brine, dried (magnesium sulfate), filtered and evaporated. Purification by filtration through a 30 g plug of flash silica gel with 95:5 ethyl acetate:ethanol gave 0.624 g (75%) of (9aSR)-7-(ethylenedioxy-2-(pyrimidin-2-yl)-2,3,4,6,7,8,9,9a-octahydro-1H-pyrido[1,2-a]pyrazine. mp (base) 121–122° C. Anal calcd for $C_{14}H_{20}N_4O_2$: C, 60.85; H, 7.29; N, 20.27; found: C, 60.84; H, 7.26; N, 20.42.

A solution of 0.60 g (2.2 mmol) of (9aSR)-7-(ethylenedioxy)-2-(pyrimidin-2-yl)-2,3,4,6,7,8,9,9a-octahydro-1H-pyrido[1,2-a]pyrimidine was dissolved in 8 mL of 6M HCl and refluxed for 3 h. The solution was cooled to room temperature, the solvent was evaporated, the residue dissolved in methylene chloride, mixed with aqueous potassium carbonate, the layers were separated, and the aqueous layer extracted with methylene chloride (2×). The combined organic phase was dried (magnesium sulfate), filtered and evaporated. Filtration through a plug of flash silica gel with 95:5 ethyl acetate:ethanol gave 0.205 g (41%) of 7-keto derivative. The 7-keto derivative was dissolved in 10 mL of methanol and treated with 0.33 g (0.88 mmol) of 10% sodium borohydride on alumina. After stirring for 1 h, the mixture was filtered and evaporated to give 0.156 g (75%) of crude 7-hydroxy derivative. The crude 7-hydroxy derivative, 0.094 g (1.0 mmol) of phenol, and 0.209 g (0.799 mmol) of triphenylphosphine were dissolved in 1.4 mL of dry THF. The mixture was treated with 0.13 mL (0.80 mmol) of diethyl azodicarboxylate and stirred at room temperature for 24 h. The mixture was diluted with ethyl ether, extracted with 0.1M HCl (3×), the combined aqueous phase was washed with ethyl ether (2×), basified with conc. ammonium hydroxide, and extracted with ethyl acetate (3×). The combined ethyl acetate layers were dried (magnesium sulfate), filtered and evaporated. Purification by flash silica gel chromatography with 50:50 ethyl acetate:hexane gave 0.036 g (17%) of the title compound. mp (base) 147–148° C. HRMS calcd for $C_{18}H_{22}N_4O$: 310.1794, found: 310.1819.

EXAMPLE 46

(4-Fluoro)phenyl-[(7RS,9aSR)-2-(pyrimidin-2-yl)-2,3,4,6,7,8,9,9a-octahydro-1H-pyrido[1,2-a]pyrazin-7-yl]-methanol

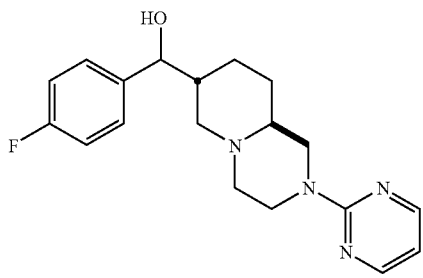

A flame-dried 3-neck flask was attached to a bleach trap and charged with 20 mL of methylene chloride and 0.77 mL (1.1 mmol) of oxalyl chloride. The solution was chilled to −78° C. and anhydrous DMSO (1.38 mL, 1.93 mmol) was added dropwise at a rate which kept the internal temperature at or below −50° C. A methylene chloride solution of (7RS,9aSR)-7-hydroxymethyl-2-(pyrimidin-2-yl)-2,3,4,6,7,8,9,9a-octahydro-1H-pyrido[1,2-a]pyrazine (2.5 g, 9.1 mmol) was added followed by slow addition of, 5.2 mL (37 mmol) of triethylamine. After warming to room temperature, 40 mL of water was added, the layers were separated and the aqueous phase extracted with methylene chloride (4×). The combined organic phase was dried (sodium sulfate), filtered and evaporated to give 2.24 g (90%) of aldehyde. $^{13}$C NMR (CDCl$_3$): δ 24.0, 28.5, 43.5, 48.8, 49.0, 55.4, 54.7, 60.3, 109.9, 157.7, 161.3, 202.3. HRMS calcd for $C_{13}H_{18}N_4O$: 246.1481, found: 246.1484.

A solution of the crude aldehyde (0.44 g, 1.6 mmol) in 45 mL of dry THF was chilled to −10° C. and treated with 8.8 mL (18 mmol, 2M in THF) of 4-fluorophenyl magnesium bromide. The solution was allowed to warm to room temperature and 10 mL of ice water was added carefully followed by 100 mL of saturated ammonium chloride. The aqueous phase was extracted with ethyl ether (1×), dried (sodium sulfate), filtered and evaporated. Purification by flash silica gel chromatography with methylene chloride:methanol:conc. ammonium hydroxide 12:1:0.04 gave 0.037 g (6.7%) of the title compound. $^{13}$C NMR (CDCl$_3$): δ 26.1, 28.8, 43.2, 43.3, 46.1, 48.8, 54.8, 57.8, 58.0, 60.9, 76.4, 109.9, 115.09, 115.38, 127.98, 128.09, 138.7, 157.7, 160.6, 161.4, 163.4. HRMS calcd for $C_{19}H_{24}FN_4O$ (MH+): 343.1934, found: 343.1938.

EXAMPLE 47

(4-Fluoro)phenyl-[(7SR,9aSR)-2-(pyrimidin-2-yl)-2,3,4,6,7,8,9,9a-octahydro-1H-pyrido[1,2-a]pyrazin-7-yl]-methanol

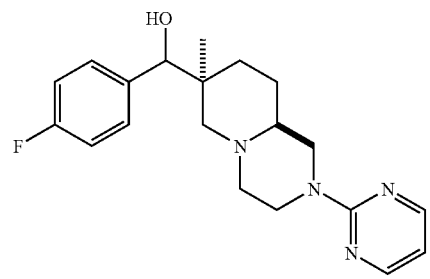

The title compound was prepared according to Example 46 starting with (7SR,9aSR)-7-hydroxymethyl-2-(pyrimidin-2-yl)-2,3,4,6,7,8,9,9a-octahydro-1H-pyrido[1,2-a]pyrazine. HRMS calcd for $C_{19}H_{24}FN_4O$ (MH+): 343.1934, found: 343.1934.

EXAMPLE 48

(4-Fluoro)phenyl-[(7RS,9aSR)-2-(pyrimidin-2-yl)-2,3,4,6,7,8,9,9a-octahydro-1H-pyrido[1,2-a]pyrazin-7-yl]-methanone

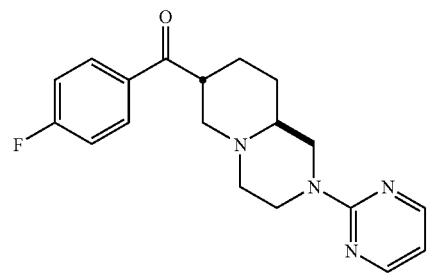

The title compound was prepared according to the oxalyl chloride/DMSO oxidation step of Example 46 starting with (4-fluoro)phenyl-[(7RS,9aSR)-2-(pyrimidin-2-yl)-2,3,4,6,7,8,9,9a-octahydro-1H-pyrido[1,2-a]pyrazin-7-yl]-methanol (Example 46). $^{13}$C NMR (CDCl$_3$): δ 27.3, 28.3, 48.6, 54.1, 56.7, 59.9, 110.1, 115.77, 116.05, 131.20, 131.32, 132.4, 158.0, 161.1, 163.4, 166.7. HRMS calcd for C$_{19}$H$_{21}$FN$_4$O: 340.1699, found: 340.1539.

EXAMPLE 49

(7S,9aS)-7-(4-Fluorophenoxy)methyl-2-(5-fluoropyrimidin-2-yl)-2,3,4,6,7,8,9,9a-octahydro-1H-pyrido[1,2-a]pyrazine

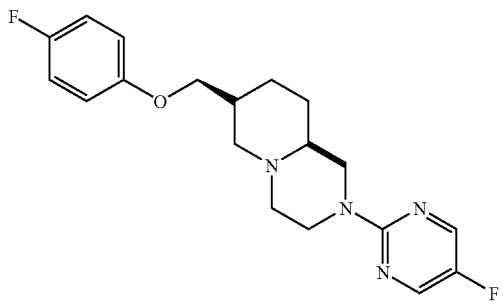

A solution of 0.82 g (3.08 mmol) of (7S,9aS)-7-hydroxymethyl-2-(5-fluoropyrimidin-2-yl)-2,3,4,6,7,8,9,9a-octahydro-1H-pyrido[1,2-a]pyrazine (Preparation 13), 0.52 g (4.62 mmol) of 4-fluorophenol, 0.97 g (3.70 mmol) of triphenylphosphine in dry THF was treated with 0.64 g (3.70 mmol) of diethyl azodicarboxylate and stirred at room temperature for 72 h. The solvent was evaporated, the residue dissolved in 50:50 ethyl acetate:ethyl ether, and treated with HCl(g) in ethyl ether until precipitation ceased. The solid was collected by filtration, dissolved in chloroform, 1M sodium hydroxide was added, and the layers were separated. The organic layer was dried (magnesium sulfate), filtered and evaporated. Purification by flash silica gel chromatography with 90:10 hexane:ethyl acetate gave 0.49 g (44%) of the title compound. mp (.HCl) 225–228° C. $^{13}$C NMR (base, CDCl$_3$): δ 24.8, 25.2, 33.8, 44.3, 49.7, 54.8, 56.6, 61.0, 69.5, 115.48, 115.53, 115.59, 115.83, 144.97, 145.26, 149.85, 153.15, 155.42, 155.54, 158.69, 158.74. HRMS calcd for C$_{19}$H$_{22}$F$_2$N$_4$O: 360.1762, found: 360.1752.

EXAMPLE 50

(7RS,9aSR)-7-(5-Fluoro-1H-indol-3-yl)methyl-2-(pyrimidin-2-yl)-2,3,4,6,7,8,9,9a-octahydro-1H-pyrido[1,2-a]pyrazine

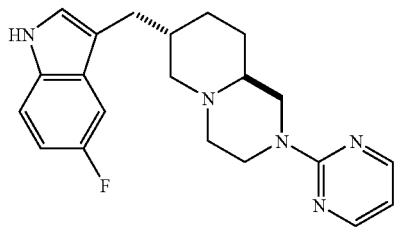

A solution of 2.22 g (8.1 mmol) of (7RS,9aSR)-7-hydroxymethyl-2-(2-pyrimidinyl)-2,3,4,6,7,8,9,9a-octahydro-1H-pyrido[1,2-a]pyrazine (Preparation 3) and triethyl amine (1.34 mL, 9.7 mmol) in 15 mL of methylene chloride was chilled to 0° C. and treated with a solution of 0.64 mL (8.3 mmol) of methanesulfonyl chloride in 7 mL of methylene chloride. The solution was stirred at 0° C. for 1 h, and then allowed to warm to room temperature. Water was added (30 mL), and the pH adjusted to 9.5 with 2M sodium hydroxide. The layers were separated and the aqueous phase extracted with methylene chlorde (30 mL). The combined organic phase was dried (sodium sulfate), filtered and evaporated to give 2.05 g (78%) of mesylate.

A flame-dried flask was charged with 0.2 g (1.5 mmol) of 5-fluoroindole, 8 mL of benzene and 0.49 mL (1.5 mmol) of ethyl magenesium bromide (3M in THF). Under vigorous stirring, the above mesylate (0.53 g, 1.6 mmol) was added and the mixture stirred at room temperature for, 18 h. Water (15 mL), ethyl acetate (10 mL) and sat. sodium bicarbonate were added, and the layers were separated. The organic phase was dried (sodium sulfate), filtered and evaporated. Initial purification by flash silica gel chromatography with ethyl acetate:methanol 95:5 followed a second purification by flash silica gel chromatography with 30:70:2 ethyl acetate:hexane:methanol gave 80 mg of the title compound. $^{13}$C NMR (CDCl$_3$): δ 29.5, 30.2, 30.8, 37.1, 43.6, 49.1, 54.8, 60.9, 103.8, 104.1, 109.0, 109.4, 109.8, 110.7, 110.9, 114.4, 114.5, 123.7, 132.8, 156.1, 157.7, 159.2, 161.5. HRMS calcd for C$_{21}$H$_{24}$FN$_5$: 365.2011, found: 365.1985.

EXAMPLE 51

(7RS,9aSR)-7-(5-Fluoro-1-methyl-1H-indol-3-yl)methyl-2-(pyrimidin-2-yl)-2,3,4,6,7,8,9,9a-octahydro-1H-pyrido[1,2-a]pyrazine

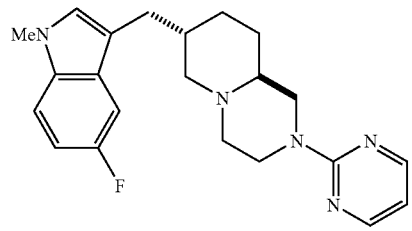

A flame-dried flask was charged with 0.103 g (0.28 mmol) of (7RS,9aSR)-7-(5-fluoro-1H-indol-3-yl)methyl-2-(pyrimidin-2-yl)-2,3,4,6,7,8,9,9a-octahydro-1H-pyrido[1,2-a]pyrazine (Example 50), anhydrous DMF (1 mL) and 12 mg (0.30 mmol) of sodium hydride (60% oil dispersion). The suspension was treated with 0.019 mL (0.31 mmol) of methyl iodide and the mixture was heated at 50° C. for 16 h. The mixture was cooled to room temperature, concentrated in vacuo, and diluted with methylene chloride (25 mL) and water (25 mL), and the layers were separated. The organic phase was dried (sodium sulfate), filtered and evaporated to a solid residue. The solid was washed with ethyl acetate (2×), the ethyl acetate was evaporated to give 50 mg of the title compound. $^1$H NMR (CDCl$_3$): δ 1.00–1.31 (m, 3H), 1.64–2.23 (m, 6H), 2.54–3.1 (m, 5H), 3.69 (s, 3H), 4.51–4.56 (m, 2H), 6.43 (dd, J=1 Hz, 1H), 6.83 (s, 1H), 6.93 (m, 1H), 7.15 (m, 2H), 8.27 (d, J=1 Hz, 2H). TLC R$_f$: 0.81 (90:10:1 methylene chloride:methanol:ammonium hydroxide).

EXAMPLE 52

(7RS,9aSR)-7-(5-Chloro-and-(6-Chloro-2-methyl-benzoimidazol-1-yl)methyl-2-(pyrimidin-2-yl)-2,3,4,6,7,8,9,9a-octahydro-1H-pyrido[1,2-a]pyrazine

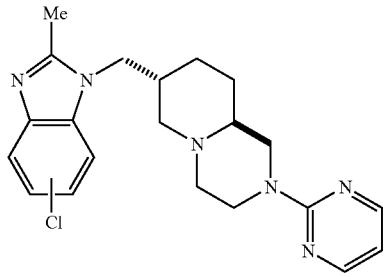

A solution of 2.22 g (8.1 mmol) of (7RS,9aSR)-7-hydroxymethyl-2-(pyrimidin-2-yl)-2,3,4,6,7,8,9,9a-octahydro-1H-pyrido[1,2-a]pyrazine (Preparation 3) and triethyl amine (1.34 mL, 9.7 mmol) in 15 mL of methylene chloride was chilled to 0° C. and treated with a solution of 0.64 mL (8.3 mmol) of methanesulfonyl chloride in 7 mL of methylene chloride. The solution was stirred at 0° C. for 1 h, and then allowed to warm to room temperature. Water was added (30 mL). and the pH adjusted to 9.5 with 2M sodium hydroxide. The layers were separated and the aqueous phase extracted with methylene chlorde (30 mL). The combined organic phase was dried (sodium sulfate), filtered and evaporated to give 2.05 g (78%) of mesylate.

A flame-dried flask was charged with 0.11 g (0.67 mmol) of 5-chloro-2-methylbenzimidazole, 3 mL of dry DMF, and 29 mg (0.74 mmol) of sodium hydride (60% oil dispersion). The solution heated at 50° C. for 30 min, and then cooled to room temperature. The above mesylate (0.20 g, 0.61 mmol) was added and the mixture was heated at 100° C. for 16 h. The mixture was cooled to room temperature, and concentrated in vacuo. Ethyl acetate (30 mL) and water (30 mL) were added, the layers were separated, and the organic phase was dried (sodium sulfate), filtered and evaporated. Purification by flash silica gel chromatography with ethyl acetate gave 130 mg of a mixture of the title compounds. $^1$H NMR (CDCl$_3$): δ 1.2 (m, 2H), 1.9 (m, 5H), 2.2 (m,2H), 2.5 (s, 3H), 2.75 (m, 2H), 2.95 (m, 1H), 3.85 (m, 2H), 4.55 (m, 2H), 6.45 (dd, J=1 Hz, 1H), 7.1 (s, 1H), 7.2 (m, 1H), 7.4 (m, 1H), 8.25 (d, J=1 Hz, 2H). TLC R$_f$: 0.32 (90:10 methylene chloride: methanol). HRMS calcd for C$_{21}$H$_{25}$ClN$_6$: 396.1829, found: 396.1809.

EXAMPLE 53

1-(4-Fluorophenyl)-2-[(7RS,9aSR)-2-(pyrimidin-2-yl)-2,3,4,6,7,8,9,9a-octahydro-1H-pyrido[1,2-a]pyrazin-7-yl]-ethanol

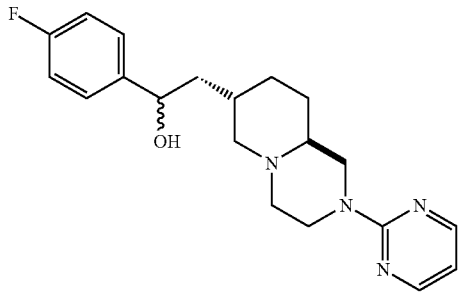

A solution of 2.2 g (8.1 mmol) of (7RS,9aSR)-7-hydroxymethyl-2-(pyrimidin-2-yl)-2,3,4,6,7,8,9,9a-octahydro-1H-pyrido[1,2-a]pyrazine and 1.3 mL (9.7 mmol) of triethylamine in 15 mL of methylene chloride at 0° C. was treated with a solution of 0.64 mL (8.3 mmol) of methanesulfonyl chloride in 7 mL of methylene chloride, and the solution was stirred for 1 h. Water was added (30 mL) and the pH adjusted to 9.5 with 2M sodium hydroxide. The layers were separated, the aqueous phase was extracted with methylene chloride (30 mL), the combined organic phase was dried (sodium sulfate), filtered and evaporated to give 2.05 g (78%) of mesylate.

The above mesylate (2.05 g 6 mmol) was dissolved in 50 mL of dry DMF, 0.31 g (6 mmol) of sodium cyanide was added and the mixture heated at 110° C. under a nitrogen atmosphere for 16 h. The reaction was cooled to room temperature, 1 mL of saturated sodium carbonate solution was added. The solvent was removed in vacuo, the residue was taken up in ethyl-acetate (100 mL) and water (50 mL), and the layers were separated. The organic layer was washed with sat. sodium carbonate (2×), dried (sodium sulfate), filtered and evaporated to give 1.4 g (91%) of nitrile. HRMS calcd for C$_{14}$H$_{19}$N$_5$: 257.1640, found: 257.1630.

A flame-dried flask containing 0.350 g (1.36 mmol) of the above nitrile was charged with 1.8 mL (1.8 mmol) of 1M diisobutylaluminum hydride. The solution was stirred for 2 h at room temperature, then stirred at 50° C. for 1 h. The reaction was cooled to room temperature, and 2M hydrochloric acid was added slowly until gas evolution ceased. The pH was adjusted to 8 with 2M sodium hydroxide, and the mixture was diluted with 50 mL of ethyl ether and 50 mL of water. The layers were separated, the organic phase was dried (sodium sulfate), filtered and evaporated. Purification by flash silica gel chromatography with 18:1:0.04 methylene chloride:methanol:conc. ammonium hydroxide gave 31 mg (9%) of aldehyde.

A flame dried flask containing 30 mg (0.10 mmol) of the above aldehyde in 1 mL of dry THF was chilled to −10° C. and 0.075 mL (0.15 mmol) of 4-fluorophenyl magnesium bromide (2M in THF) was added. The reaction was allowed to warm to room temperature and stirred for 1 h. Water (1 mL), saturated ammonium chloride (1 mL) and ethyl ether (5 mL) were added, and the layers were separated. The organic phase was dried (sodium sulfate), filtered and evaporated. Purification by flash silica gel chromatography with 24:1:0.04 methylene chloride:methanol:conc. ammonium hydroxide gave 11 mg (39%) of the title compound. $^1$H NMR (CDCl$_3$): δδ 0.97–1.05 (m, 1H), 1.23–1.61 (m, 2H), 1.64–1.86 (m 6H), 2.14–2.23 (m, 1H), 2.54–2.78 (m, 1H), 2.81–3.02 (m, 3H), 4.49–4.61 (m, 2H), 4.77–4.71 (m, 1H), 6.45 (t, J=1 Hz, 1H), 6.97–7.03 (m, 2H), 7.25–7.32 (m, 2H), 8.27 (d, J=1 Hz, 2H). HRMS calcd for C$_{20}$H$_{25}$FN$_4$O: 356.2012, found: 356.2009.

EXAMPLE 54

1-(4-Fluorophenyl)-2-[(7SR,9aSR)-2-(pyrimidin-2-yl)-2,3,4,6,7,8,9,9a-octahydro-1H-pyrido[1,2-a]pyrazin-7-yl]-ethanone

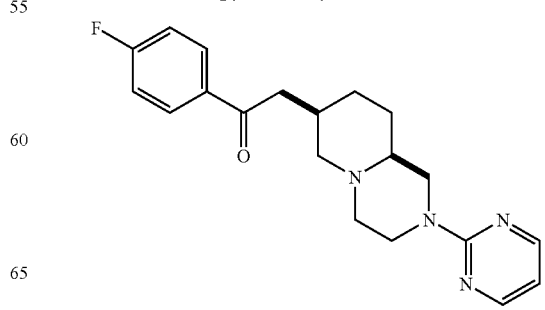

A solution of 38.1 g (117 mmol) of (7SR,9aSR)-7-(methanesulfonyloxy)methyl-2-(pyrimidin-2-yl)-2,3,4,6,7,8,9,9a-octahydro-1H-pyrido[1,2-a]pyrazine (prepared according to U.S. Pat. No. 5,122,525) and 6.01 g (122 mmol) of sodium cyanide in 500 mL of dry DMF was heated at 110° C. for 16 h. The mixture was cooled to room temperature, 10 mL of saturatic sodium bicarbonate was added and the mixture concentrated in vacuo. Water (1000 mL) and ethyl acetate (1000 mL) were added to the solid residue, the pH was adjusted to 11, and the layers were separated. The organic phase was washed with water (2×), dried (sodium sulfate), filtered and evaporated. Recrystalization from ethyl acetate-hexane gave 14.5 g of [(7SR,9aSR)-2-(pyrimidin-2-yl)-2,3,4,6,7,8,9,9a-octahydro-1H-pyrido[1,2-a]pyrazin-7-yl]acetonitrile. $^{13}$C NMR (CDCl$_3$): d 19.5, 24.1, 26.9, 31.3, 33.1, 43.6, 48.9, 54.5, 109.8, 119.8, 157.7, 161.4.

A solution of 0.200 g (0.78 mmol) of [(7SR,9aSR)-2-(pyrimidin-2-yl)-2,3,4,6,7,8,9,9a-octahydro-1H-pyrido[1,2-a]pyrazin-7-yl]acetonitrile in 4 mL of dry THF was treated with 4.3 mg (0.03 mmol) of cuprous bromide and 0.85 mL (0.85 mmol) of 4-fluorophenyl magnesium bromide (1M in THF), and the mixture was refluxed for 48 h. The mixture was cooled to room temperature, 0.75 mL of water was added carefully followed by 3.5 mL of 15% sulfuric acid. The mixture was refluxed for 24 h. The reaction was cooled to room temperature, and 10% sodium carbonate solution was added until gas evolution ceased. Ethyl ether (10 mL) was added, the layers were separated, and the aqueous phase was extracted with ethyl ether (2×10 mL). The combined organics were dried (sodium sulfate), filtered and evaporated. Purification by flash silica gel chromatography with ethyl acetate:hexane:methanol:conc. ammonium hydroxide (1:1:0.01:0.01) gave 30 mg of the title compound. $^{13}$C NMR (CDCl$_3$): d 25.1, 28.3, 29.9, 40.2, 43.7, 49.1, 54.8, 59.1, 61.1, 109.7, 115.4, 115.7, 130.8, 130.9, 134.0, 157.7, 161.5, 164.0, 167.4. HRMS calcd for C$_{20}$H$_{23}$FN$_4$O: 354.1856, found: 354.1847.

EXAMPLE 55

(7S,9aS)-7-(Substituted-phenoxy)methyl-2-(5-fluoropyrimidin-2-yl)-2,3,4,6,7,8,9,9a-octahydro-1H-pyrido[1,2-a]pyrazines

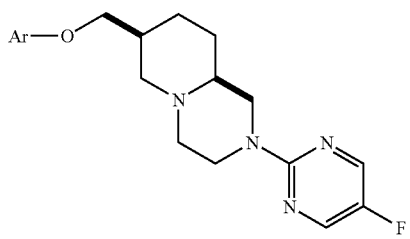

Compounds of the above formula were prepared according to Example 49 using (7S,9aS)-7-hydroxymethyl-2-(5-fluoropyrimidin-2-yl)-2,3,4,6,7,8,9,9a-octahydro-1H-pyrido[2-a]pyrazine (Preparation 13) and the appropriate phenol. Purification was generally accomplished with flash silica gel chromatography using mixtures of ethyl acetate and hexane as the eluting solvent. The stereochemical configuration, 7-(substituted-phenoxy)methyl substituent, melting point of the monohydrochloride salt, and HRMS data are shown.

EXAMPLE 55a (7S,9aS)-7-(4-Fluoro-2-methyl-phenoxy)methyl; mp 237–243° C.; HRMS calcd for C$_{20}$H$_{24}$F$_2$N$_4$O: 374.1913, found: 374.1874.

EXAMPLE 55b (7S,9aS)-7-(3-Cyano-phenoxy)methyl-; mp 209–211° C.; HRMS calcd for C$_{20}$H$_{23}$FN$_5$O (MH+): 368.1887, found: 368.1884.

EXAMPLE 55c (7S,9aS)-7-(3-(Carbomethoxy)methyl-phenoxy)methyl-; mp 158–161° C.; HRMS calcd for C$_{22}$H$_{28}$FN$_4$O$_3$(MH+): 415.2139, found: 415.2123.

EXAMPLE 56

(7S,9aS)-7-(Substitued-phenoxy)methyl-2-(5-fluoropyrimidin-2-yl)-2,3,4,6,7,8,9,9a-octahydro-1H-pyrido[1,2-a]pyrazines

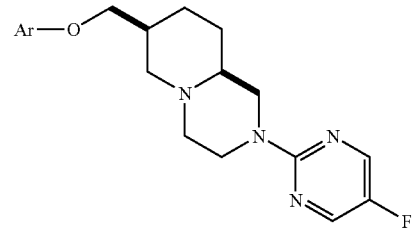

The following compounds were prepared according to Example 8 from (7S,9aS)-7-hydroxymethyl-2-(5-fluoropyrimidin-2-yl)-2,3,4,6,7,8,9,9a-octahydro-1H-pyrido[1,2-a]pyrazine (Preparation 13) and the appropriate phenol. Purification was generally accomplished by flash silica gel chromatography using mixtures of ethyl acetate and hexane or mixtures of chloroform and methanol as the eluting solvent. The stereochemical configuration, 7-(substituted-phenoxy)methyl substituent, melting point of the monohydrochloride salt and HRMS data are shown.

EXAMPLE 56a (7S,9aS)-7-(4-Fluoro-2-trifluoromethylphenoxy)methyl; mp 205–206° C.; HRMS calcd for C$_{20}$H$_{21}$F$_5$N$_4$O: 428.1636, found: 428.1633.

EXAMPLE 56b (7S,9aS)-7-(2-Bromo4-fluorophenoxy)methyl; mp 228–230° C.; HRMS calcd for C$_{19}$H$_{21}$BrF$_2$N$_4$O: 438.0867, found: 438.0862.

EXAMPLE 56c (7S,9aS)-7-(2-Carbomethoxy-4-fluorophenoxy)methyl; mp 204–205° C.; HRMS calcd for C$_{21}$H$_{24}$F$_2$N$_4$O$_3$: 418.1816, found: 418.1836.

EXAMPLE 56d (7S,9aS)-7-(3,4-Difluorophenoxy)methyl-; mp 226–227° C.; HRMS calcd for $C_{19}H_{21}F_3N_4O$: 378.1667, found: 378.1640.

EXAMPLE 56e (7S,9aS)-7-(3,5-Difluorophenoxy)methyl-; mp 208–211° C.; HRMS calcd for $C_{19}H_{21}F_3N_4O$: 378.1667, found: 378.1703.

EXAMPLE 56f (7S,9aS)-7-(3-Trifluoromethoxyphenoxy)methyl-; mp 180–184° C.; HRMS calcd for $C_{20}H_{23}F_4N_4O_2$ (MH+): 427.1757, found: 427.1776.

EXAMPLE 56g (7S,9aS)-7-(4-Trifluoromethylphenoxy)methyl-; mp 188–193° C.; HRMS calcd for $C_{20}H_{23}F_4N_4O$ (MH+): 411.1803, found: 411.1803.

EXAMPLE 56h (7S,9aS)-7-(3-Methoxyphenoxy)methyl-; mp 229–103° C.; HRMS calcd for $C_{20}H_{26}FN_4O_2$ (MH+): 373.2040, found: 373.2051.

EXAMPLE 56i (7S,9aS)-7-(4-Methoxyphenoxy)methyl-; mp 220–224° C.; HRMS calcd for $C_{20}H_{26}FN_4O_2$ (MH+): 373.2040, found: 373.2055.

EXAMPLE 56j (7S,9aS)-7-(4-Ethylphenoxy)methyl-; mp 227–229° C.; HRMS calcd for $C_{21}H_{28}FN_4O$ (MH+): 371.2247, found: 371.2228.

EXAMPLE 56k (7S,9aS)-7-(2,4-Difluorophenoxy)methyl-; mp 222–224° C.; HRMS calcd for $C_{19}H_{22}F_3N_4O$ (MH+): 379.1746, found: 379.1759.

EXAMPLE 56l (7S,9aS)-7-(4-Carboexthoxy-phenoxy)methyl-; mp 230–232° C.; HRMS calcd for $C_{22}H_{28}FN_4O_3$ (MH+): 415.2145, found: 415.2130.

EXAMPLE 56m (7S,9aS)-7-(4-Bromo-2-methoxy-phenoxy)methyl-; mp 214–216° C.; HRMS calcd for $C_{20}H_{25}BrFN_4O_2$ (MH+): 451.1145, found: 451.1108.

EXAMPLE 56n (7S,9aS)-7-(3,4,5-Trifluoro-phenoxy)methyl-; mp 188–191° C.; HRMS calcd for $C_{19}H_{21}F_4N_4O$ (MH+): 397.1651, found: 397.1667.

EXAMPLE 56o (7S,9aS)-7-(3-Nitro-phenoxy)methyl-; mp 114–119° C.; HRMS calcd for $C_{19}H_{23}FN_5O_3$(MH+): 388.1785, found: 388.1799.

EXAMPLE 56p (7S,9aS)-7-(3-Acetamido-phenoxy)methyl-; mp 162–165° C.; HRMS calcd for $C_{21}H_{27}FN_5O_2$ (MH+): 400.2149, found: 400.2131.

EXAMPLE 56q (7S,9aS)-7-(3-Trifluoromethyl-phenoxy)methyl-; mp 200–202° C.; HRMS calcd for $C_{20}H_{23}F_4N_4O$ (MH+): 411.1808, found: 411.1781.

EXAMPLE 56r (7S,9aS)-7-(3-Carbomethoxy-phenoxy)methyl-; mp 225–226° C.; HRMS calcd for $C_{21}H_{26}FN_4O_3$ (MH+): 401.1989, found: 401.1989.

EXAMPLE 56s (7S,9aS)-7-(3-(4-Morpholino)-phenoxy)methyl-; mp 233–236° C.; HRMS calcd for $C_{23}H_{31}FN_5O_2$ (MH+): 428.2462, found: 428.2477.

EXAMPLE 56t (7S,9aS)-7-(3-(1,1-Dimethyl)ethyl-phenoxy)methyl-; mp 252–254° C.; HRMS calcd for $C_{23}H_{32}FN_4O$ (MH+): 399.2560, found: 399.2528.

EXAMPLE 56u (7S,9aS)-7-(4-Fluoro-2-propyl-phenoxy)methyl-; mp 165–170° C.; HRMS calcd for $C_{22}H_{28}F_2N_4O$: 402.2225, found: 402.2183.

EXAMPLE 56v (7S,9aS)-7-(3-Methyl-phenoxy)methyl-; mp 90–92° C.; HRMS calcd for $C_{20}H_{26}FN_4O$ (MH+): 357.2091, found: 357.2088.

EXAMPLE 56w (7S,9aS)-7-(3-Dimethylamino-phenoxy)methyl-; mp 216–220° C. (dec); HRMS calcd for $C_{21}H_{29}FN_5O$ (MH+): 386.2356, found: 386.2368.

EXAMPLE 56x (7S,9aS)-7-(2-Methoxy-3-(1-methyl)ethyl-phenoxy)methyl-; mp 221–223° C. (dec); HRMS calcd for $C_{23}H_{32}FN_4O_2$ (MH+): 415.2505, found: 415.2467.

EXAMPLE 56y (7S,9aS)-7-(4-Acetamido-phenoxy)methyl-; mp 220–223° C.; HRMS calcd for $C_{21}H_{27}FN_5O_2$ (MH+): 400.2143, found: 400.2136.

EXAMPLE 57

(7S,9aS)-7-(Substitued-phenoxy)methyl-2-(5-chloro-pyridin-2-yl)-2,3,4,6,7,8,9,9a-octahydro-1H-pyrido[1,2-a]pyrazines

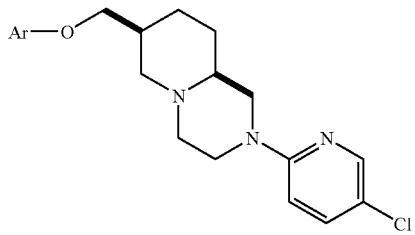

Compounds of the above formula were prepared according to EXAMPLE 8 from (7S,9aS)-7-hydroxymethyl-2-(5-chloropyridin-2-yl)-2,3,4,6,7,8,9,9a-octahydro-1H-pyrido[1,2-a]pyrazine (Preparation 14) and the appropriate phenol. Purification was generally accomplished by flash silica gel chromatography using mixtures of ethyl acetate and hexane or mixtures of, chloroform and methanol as the eluting solvent. The stereochemical configuration, 7-(substituted-phenoxy)methyl substituent, melting point of the monohydrochloride salt and HRMS data are shown.

EXAMPLE 57a (7S,9aS)-7-(4-Fluorophenoxy)methyl; mp 244–249° C.; HRMS calcd for $C_{20}H_{23}ClFN_3O$: 375.1508, found:. 375.1490.

EXAMPLE 57b (7S,9aS)-7-(3,5-Difluorophenoxy)methyl; mp 230–233° C.: HRMS calcd for $C_{20}H_{22}ClF_2N_3O$: 393.1414, found: 393.1389.

Preparation 1

(7R,9aS)-7-Hydroxymethyl-2,3,4,6,7,8,9,9a-octahydro-1H-pyrido[1,2-a]pyrazine.2HCl

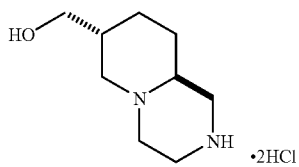

A solution of 4.0 g (15 mmol) (7R,9aS)-2-BOC-7-hydroxymethyl-2,3,4,6,7,8,9,9a-octahydro-1H-pyrido[1,2-a]pyrazine (WO 93/25552) in 40 mL of chloroform was treated with excess HCl(g) in ether. After stirring for 1 h, the solvent was evaporated to give 3.1 g (86%) of the hygroscopic dihydrochloride salt which was used without further purification in subsequent reactions. $^{13}C$ NMR (.2 HCl, d-$_6$ DMSO): δ 26.9, 28.8, 30.5, 44.9, 50.6, 54.7, 59.0, 61.1, 64.5. HRMS calcd for $C_9H_{18}N_2O$: 170.1419, found: 170.1414.

Preparation 2

(7S,9aS)-7-Hydroxymethyl-2,3,4,6,7,8,9,9a-octahydro-1H-pyrido[1,2-a]pyrazine

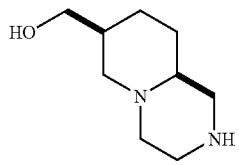

A solution of 5.84 g (21.6 mmol) of (7S,9aS)—N—BOC-7-hydroxymethyl-2,3,4,6,7,8,9,9a-octahydro-1H-pyrido[1,2-a]pyrazine (WO 93/25552) in 140 mL of trifluoroacetic acid and 60 mL of water was stirred at room temperature for 16 h. The mixture was concentrated and the residue dissolved in water. The aqueous phase saturated with solid sodium carbonate and extracted with chloroform (3×). The combined organic layers were dried (magnesium sulfate), filtered and evaporated to give 3.39 g (92%) of the title compound. This material was used without further purification for subsequent reactions. $^{13}C$ NMR (base, d-$_6$ DMSO): δ 24.8, 25.1, 36.0, 45.7, 51.9, 56.1, 56.7, 62.0, 62.7.

Preparation 3

(7RS,9aSR)-7-Hydroxymethyl-2-(pyrimidin-2-yl)-2,3,4,6,7,8,9,9a-octahydro-1H-pyrido[1,2-a]pyrazine

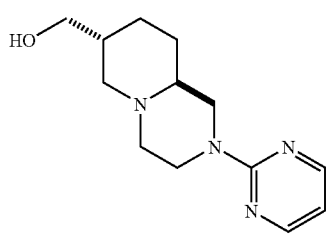

A mixture of 4.5 g (26 mmol) of (7RS,9aSR)-7-hydroxymethyl-2,3,4,6,7,8,9,9a-octahydro-1H-pyrido[1,2-a]pyrazine (U.S. Pat. No. 5,326,874), 3.0 g (26 mmol) of 2-chloropyrimidine, and 6.7 g (63 mmol) of sodium carbonate in 100 mL of water is heated at 95° C. for 16 h. The mixture was cooled to room temperature, extracted with methylene chloride (3×), the combined organic layers were washed with water and brine, dried, filtered and evaporated to give 4.68 g (72%) of the title compound which was used without purification in subsequent reactions.

Preparation 4

(7R,9aS)-7-Hydroxymethyl-2,3,4,6,7,8,9,9a-octahydro-2-(pyrimidin-2-yl)-1H-pyrido[1,2-a]pyrazine

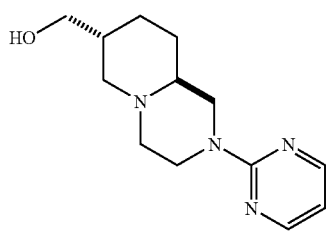

A mixture of 2.52 g (14.8 mmol) of (7R,9aS)-7-hydroxymethyl-2,3,4,6,7,8,9,9a-octahydro-1H-pyrido[1,2-a]

pyrazine (Preparation 1), 1.70 g (14.8 mmol) of 2-chloropyrimidine and 6.91 g (65.2. mmol) of sodium carbonate in 150 mL of water was heated at 90° C. for 16 h.; then cooled and extracted with chloroform (3×). The organic layer was dried (magnesium sulfate), filtered and evaporated to give 3.25 g (89%) of the title compound which was used without purification in subsequent reactions.

Preparation 5

(7R,9aS)-7-Hydroxymethyl-2-(5-fluoropyrimidin-2-yl)-2,3,4,6,7,8,9,9a-octahydro-1H-pyrido[1,2-a]pyrazine

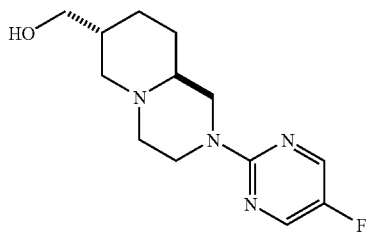

A solution of 4.41 g (18.2 mmol) of (7R,9aS)-7-hydroxymethyl-2,3,4,6,7,8,9,9a-octahydro-1H-pyrido[1,2-a]pyrazine dihyrochloride (Preparation 1), 3.78 g (28.5 mmol) of 2-chloro-5-fluoropyrimidine (B. Baasner, E. Klauke *J. Fluroine Chem.*, 1989, 45, 417–430), and 9.07 g (85.6 mmol) of sodium carbonate in 180 mL of water were heated at 95° C. for 16 h. The mixture was cooled to room temperature, extracted with chloroform (2×), dried (magnesium sulfate), filtered and evaporated. Purification by flash chromatography on silica gel using 95:5 chloroform:methanol gave 5.56 g (81%) of title compound. mp 148–149.5° C. $^{13}$C NMR (CDCl$_3$): δ 26.8, 29.0, 39.1, 44.2, 49.7, 54.8, 58.7, 60.8, 66.2, 145.0, 145.3, 149.9, 153.2, 158.7. Anal calcd for C$_{13}$H$_{19}$FN$_4$O: C, 58.63; H, 7.19; N, 21.04; found: C, 58.36; H, 7.18; N, 20.87

Preparation 6

(7RS,9aSR)-7-Hydroxymethyl-2,3,4,6,7,8,9,9a-octahydro-2-(5-fluoro-4-thiomethylpyrimidin-2-yl)-1H-pyrido[1,2-a]pyrazine

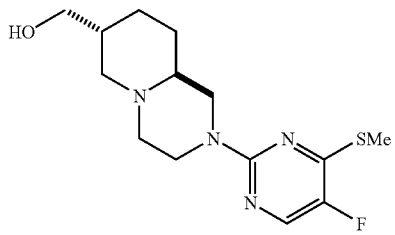

The title compound was synthesized according to Preparation 5 from (7RS,9aSR)-7-hydroxymethyl-2,3,4,6,7,8,9,9a-octahydro-1H-pyrido[1,2-a]pyrazine (U.S. Pat. No. 5,326,874) and 2-chloro-5-fluoro4-thiomethylpyrimidine (Uchytilova, V.; Holy, A.; Cech, D.; Gut, *J. Coll. Czech. Chem. Commun.*, 1975, 40, 2347. Ueda, T.; Fox, J. J., *J. Med. Chem.*, 1963. 6, 697), and was used for subsequent reactions without purification.

Preparation 7

(7R,9aS)-2-BOC-7-(4-Fluorophenoxy)methyl-2,3,4,6,7,8,9,9a-octahydro-1H-pyrido[1,2-a]pyrazine

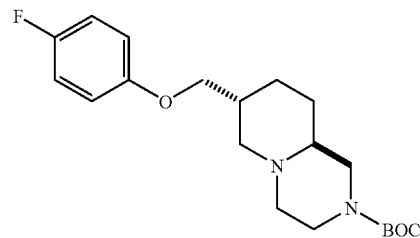

A solution of 12.0 g (44.4 mmol) of (7R,9aS)-2-BOC-7-hydroxymethyl-2,3,4,6,7,8,9,9a-octahydro-1H-pyrido[1,2-a]pyrazine (WO 93/25552), 7.47 g (66.7 mmol) of 4-fluorophenol, 14.0 g (53.3 mmol) of triphenylphosphine in 450 mL of THF was treated with 8.40 mL (53.3 mmol) of diethyl azodicarboxylate and stirred at room temperature for 16 h. The mixture was diluted with ethyl acetate and treated with HCl(g) in ethyl ether until precipitation ceased. The solvent was evaporated and the solid residue was repeatedly washed with 1:1 ethyl acetate:ethyl ether. The residue was dissolved in chloroform and washed with 15% NaOH. The organic phase was dried (magnesium sulfate), filtered and evaporated to give 15.9 g of yellow-white crystals. The crude product was dissolved in 1:1 hexane:ethyl acetate and filtered through a plug of silica gel to give 13.3 g (82%) of the title compound. mp 90–92° C. $^{13}$C NMR (CDCl$_3$): δ 26.9, 28.4, 28.8, 54.8, 58.7, 60.8, 71.6, 79.7, 115.33, 115.44, 115.58, 115.89, 154.6, 155.1, 155.6, 158.8. Anal calcd for C$_{20}$H$_{29}$FN$_2$O$_3$: C, 65.91; H, 8.02; N, 7.69; found: C, 65.90; H, 8.06; N, 7.77.

Preparation 8

(7R,9aS)-7-(4-Fluorophenoxy)methyl-2,3,4,6,7,8,9,9a-octahydro-1H-pyrido[1,2-a]pyrazine

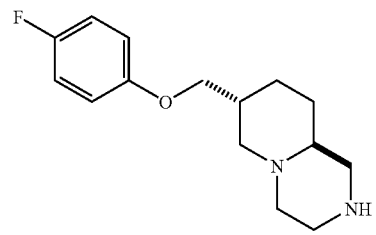

A solution of 44.4 g (122 mmol) of (7R,9aS)-2-BOC-7-(4-fluorophenoxy)methyl-2,3,4,6,7,8,9,9a-octahydro-1H-pyrido[1,2-a]pyrazine (Preparation 7) in 500 mL of trifluoroacetic acid and 200 mL of water was stirred at room temperature for 16 h. The mixture was concentrated by evaporation, the residue dissolved in water, basified with 15% NaOH, and extracted with ethyl acetate (2×). The organic layers were dried (magnesium sulfate), filtered and evaporated to give 31.4 g (96%) of (7R,9aS)-7-(4-fluorophenoxy)methyl-2,3,4,6,7,8,9,9a-octahydro-1H-pyrido[1,2-a]pyrazine which was suitable for use in subsequent reactions. Purification of a 0.40 g sample by flash silica gel chromatography eluting with 90:10 chloroform:methanol gave 0.38 g of colorless crystals. mp (.2 HCl) 200–201° C. $^{13}$C NMR (base, CDCl$_3$): δ 27.2, 29.1, 36.3, 45.9, 51.9, 56.0, 59.1, 62.5, 71.7, 115.4 (d, J$_{CF}$=8). 115.7 (d, J$_{CF}$=23). HRMS calcd for C$_{15}$H$_{21}$FN$_2$O: 264.1638, found: 264.1660.

Preparation 9

(7S,9aR)-7-(4-Fluorophenoxy)methyl-2,3,4,6,7,8,9,9a-octahydro-1H-pyrido[1,2-a]pyrazine .2HCl

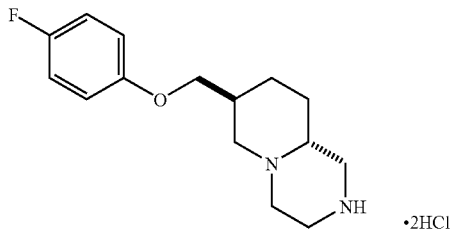

A solution of 0.39 g (1.4 mmol) of (7S,9aR)-2-BOC-7-hydroxymethyl-2,3,4,6,7,8,9,9a-octahydro-1H-pyrido[1,2-a]pyrazine, 0.24 g (2.2 mmol) of 4-fluorophenol and 0.45 g (1.7 mmol) of triphenyl phosphine in 20 mL of dry THF was treated with 0.27 mL (1.7 mmol) of diethyl azodicarboxylate, and stirred at ambient temperature for 16 h. The solution was diluted with ethyl acetate and treated with, excess HCl(g) in ethyl ether. The solvent was evaporated and the white, solid residue was washed with 1:1 ethyl acetate:ethyl ether. The solid remaining was :dissolved in chloroform and washed with 1M NaOH, dried (magnesium sulfate), filtered and evaporated to give 0.45 g of (7S,9aR)-2-BOC-7-(4-fluorophenoxy)methyl-2,3,4,6,7,8,9,9a-octahydro-1H-pyrido[1,2-a]pyrazine.

A solution of 0.44 g (1.2 mmol) of (7S,9aR)-2-BOC-7-(4-fluorophenoxy)methyl-2,3,4,6,7,8,9,9a-octahydro-1H-pyrido[1,2-a]pyrazine in 25 mL of chloroform was treated with excess HCl(g) in ethyl ether and stirred at ambient temperature for 2 h. The solvent was evaporated to give 0.40 g of title compound as the dihydrochloride salt which was used for subsequent reactions without purification.

Preparation 10

(7R,9aR)-7-(4-Fluorophenoxy)methyl-2,3,4,6,7,8,9,9a-octahydro-1H-pyrido[1,2-a]pyrazine

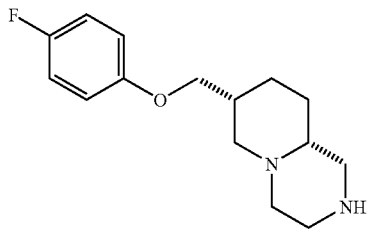

A solution of 0.71 g (2.63 mmol) of (7R,9aR)-2-BOC-7-hydroxymethyl-2,3,4,6,7,8,9,9a-octahydro-1H-pyrido[1,2-a]pyrazine, 0.44 g (3.94 mmol) of 4-fluorophenol and 0.83 g (3.16 mmol) of triphenylphosphine in 25 mL of THF was treated with 0.50 mL (3.16 mmol) of diethyl azodicarboxylate and stirred at ambient temperature for 16 h. The solvent was evaporated, the residue dissolved in ethyl acetate and washed with 1M NaOH (2×). The organic layer was dried (magnesium sulfate), filtered and evaporated. Purification by flash chromatography with 75:25 ethyl acetate-hexane gave 0.5 g of a sticky solid. This material was dissolved in, chloroform, washed with 1M NaOH, dried (magnesium sulfate), filtered and evaporated to give 0.20 g of (7R,9aR)-2-BOC-7-(4-fluorophenoxy)methyl-2,3,4,6,7,8,9,9a-octahydro-1H-pyrido[1,2-a]pyrazine.

A solution of 0.20 g (0.55 mmol) of (7R,9aR)-2-BOC-7-(4-fluorophenoxy)methyl-2,3,4,6,7,8,9,9a-octahydro-1H-pyrido[1,2-a]pyrazine in 10 mL of trifluoroacetic acid and 3 mL of water was stirred at ambient temperature for 4 h. The mixture was concentrated in vacuo and the residue-diluted with water. The solution was adjusted to pH 12 with 15% NaOH, and extracted with ethyl acetate (2×). The organic phase was dried (magnesium sulfate), filtered and evaporated to give 0.149 g of the title compound which was used without further purification for subsequent reactions.

Preparation 11

(7RS,9aSR)-7-Hydroxymethyl-2,3,4,6,7,8,9,9a-octahydro-2-(pyridin-2-yl)-1H-pyrido[1,2-a]pyrazine

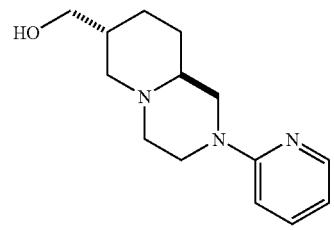

A mixture of 1.0 g (5.9 mmol) of (7RS,9aSR)-7-hydroxymethyl-2,3,4,6,7,8,9,9a-octahydro-1H-pyrido[1,2-a]pyrazine (U.S. Pat. No. 5,326,874); 4.6 9 (29 mmol) of 2-bromopyridine, 1.5 g (14 mmol) of sodium carbonate and 50 mL of isoamyl alcohol were refluxed for 18 h. The mixture was cooled to room temperature, filtered, and concentrated in vacuo. The residue was dissolved in ethyl acetate and washed with saturated sodium carbonate. The organic layer was dried (magnesium sulfate), filtered and evaporated, and the crude product was purified by flash chromatography on silica gel eluting first with chloroform followed by 95:5 chloroform:methanol to give 0.61 g (42%) of the title compound. $^{13}$C NMR (base, CDCl$_3$): δ 26.8, 29.0, 39.0, 45.1, 50.7, 54.8, 58.7, 60.8, 66.0, 107.1, 113.3, 137.5, 147.9, 159.3.

Preparation 12

3-[(7R,9aS)-2,3,4,6,7,8,9,9a-Octahydro-1H-pyrido[1,2-a]-pyrazin-7-ylmethyl]-3H-benzoxazol-2-one

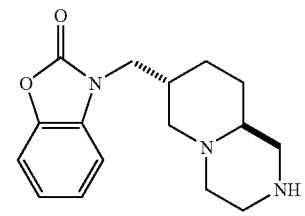

A solution of 5.0 g (18.5 mmol) of (7R,9aS)-2-BOC-7-hydroxymethyl-2,3,4,6,7,8,9,9a-octahydro-1H-pyrido[1,2-a]pyrazine (WO 93/25552) and 2.84 mL (20.4 mmol) of triethylamine in 200 mL of dry methylene, chloride was chilled to 0° C. and treated with a solution of 1.50 mL (19.4 mmol) of methanesulfonyl chloride in 75 mL of methylene chloride. After 1 h, the mixture was diluted with water, basified to pH 12 with 15% sodium hydroxide, the layers were separated, and the aqueous layer extracted with methylene chloride. The combined organic phase was washed with brine, dried (magnesium sulfate), filtered and evaporated the give 6.4 g (100%) of mesylate.

A solution of 7.00 g (51.8 mmol) of 2-benzoxazolinone in 180 mL of DMF was treated with 2.05 g (51.3 mmol) of sodium hydride (60% oil dispersion) and the mixture stirred at 50° C. for 1.5 h. The heat source was temporarily removed, a solution of 6.4 g (18 mmol) of the above mesylate in 180 mL of DMF was added and the mixture heated at 100° C. for 2 h. The reaction was cooled to room temperature, diluted with water, acidified to pH 2 with 6M hydrochloric acid and washed with ethyl acetate (2×). The pH was adjusted to 12 with conc. ammonium hydroxide and the aqueous phase extracted with ethyl acetate (3×). The combined organics were dried (magnesium sulfate), filtered and evaporated. Purification by flash silica gel chromatography with ethyl acetate gave 3.55 g (50%) of 3-[(7R,9aS) 2-BOC-2,3,4,6,7,8,9,9a-octahydro-1H-pyrido[1,2-a]-pyrazin-7-ylmethyl]-3H-benzooxazol-2-one.

A solution of 3.1 g (8.01 mmol) of 3-[(7R,9aS)-2-BOC-2,3,4,6,7,8,9,9a-octahydro-1H-pyrido[1,2-a]-pyrazin-7-ylmethyl]-3H-benzooxazol-2-one in 40 mL of chloroform was stirred with excess HCl (g) in ethyl ether for 2 h at ambient temperature. The solvent was evaporated to give 2.3 g (100%). of the title compound dihydrochloride which was used for subsequent reactions without further purification.

Preparation 13

(7S,9aS)-7-Hydroxymethyl-2-(5-fluoropyrimidin-2-yl)-2,3,4,6,7,8,9,9a-octahydro-1H-pyrido[1,2-a]pyrazine

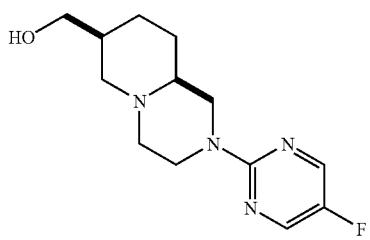

A mixture of 2.31 g (13.6 mmol) of (7S,9aS)-7-hydroxymethyl-2,3,4,6,7,8,9,9a-octahydro-1H-pyrido[1,2-a]pyrazine (Preparation 2), 1.98 g (15.0 mmol) of 2-chloro-5-fluoropyrimidine (B. Baasner, E. Klauke, *J. Fluorine Chem.*, 1989, 45, 417), 4.32 g (40.8 mmol) of sodium carbonate and 50 mL of water was heated at reflux for 16 h. The mixture was cooled to room temperature and extracted with chloroform (3×). The combined organic layers were dried (magnesium sulfate), filtered and evaporated. Purification by flash silica gel chromatography with 95:5 chloroform:methanol gave, 2.7 g (75%) of the title compound. mp (base) 111–112° C. $^{13}$C NMR (base, CDCl$_3$): δ 26.5, 27.3, 34.2, 44.3, 49.8, 54.8, 58.8, 60.7, 68.2, 145.0, 145.3, 149.9, 153.2, 158.6. HRMS calcd for $C_{13}H_{19}FN_4O$: 266.1543, found: 266.1530.

Preparation 14

(7S,9aS)-7-Hydroxymethyl-2-(5-chloropyridin-2-yl)-2,3,4,6,7,8,9,9a-octahydro-1H-pyrido[1,2-a]pyrazine

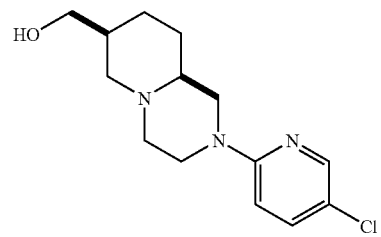

A mixture of 2.5 g (10.3 mmol) of (7S,9aS)-7-hydroxymethyl-2,3,4,6,7,8,9,9a-octahydro-1H-pyrido[1,2-a]pyrazine dihydrochloride, 7.62 g (51.5 mmol) of 2,5-dichloropyridine, 5.45 g (51.5 mmol) of sodium carbonate and 100 mL of isoamyl alcohol was heated at reflux or 72 h. The mixture was cooled, the mixture filtered to remove solids and the solvent evaporated in vacuo. Purification by flash silica gel chromatography using 95:5 chloroform:methanol gave 1.72 g (59%) of the title compound. mp (base) 61–62° C. $^{13}$C NMR (base, CDCl$_3$): δ 26.6, 27.2, 34.3, 45.4, 50.9, 54.6, 58.4, 60.5, 68.0, 107.7, 120.1, 137.1, 146.2, 157.5. HRMS calcd for $C_{14}H_{20}ClN_3O$: 281.1295, found: 281.1298.

Preparation 15

(7R,9aS)-7-Hydroxymethyl-2-(5-chloropyridin-2-yl)-2,3,4,6,7,8,9,9a-octahydro-1H-pyrido[1,2-a]pyrazine

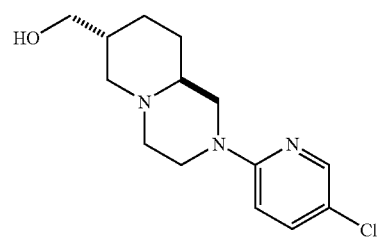

A mixture of 1.35 g (5.56 mmol) of (7R,9aS)-7-hydroxymethyl-2,3,4,6,7,8,9,9a-octahydro-1H-pyrido[1,2-a]pyrazine dihyrochloride (Preparation 1), 4.11 g (27.8 mmol) of 2,5-dichlorpyridine, 2.94 g (27.8 mmol) of sodium carbonate and 60 mL of isoamyl alcohol was heated at reflux for 48 h. The mixture was cooled and the solvent removed in vacuo. Purification by flash silica gel chromatography with 95:5 chloroform: methanol gave 1.02 g (65%) of the title compound. mp (base) 139.0–140.5° C. $^{13}$C NMR (CDCl$_3$): δ 26.8, 29.1, 39.1, 45.3, 50.8, 54.6, 58.6, 60.6, 66.2, 107.7, 120.1, 137.1, 146.2, 157.6.

The invention claimed is:

1. A pharmaceutical composition comprising an effective amount of a compound of the formula I

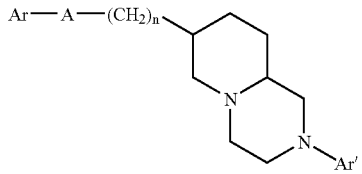

or pharmaceutically acceptable salts thereof in combination with a serotonin reuptake inhibitor, wherein
Ar is phenyl, naphthyl, benzoxazolonyl, indolyl, indolonyl, benzimidazolyl, quinolyl, furyl, benzofuryl, thienyl, benzothienyl, oxazolyl, or benzoxazolyl;
Ar is phenyl, pyridinyl, pyridazinyl, pyrimidinyl, or pyrazirmyl;
A is O, S, $SO_2$, C=O, CHOH or $(CR^3R^4)$—;
n is 0, 1 or 2;
each of Ar and $Ar^1$ may be independently and optionally substituted with one to four substiLuents independently selected from the gwup consisting of fluoro, chioro, bromo, iodo, cyano, nitro, thiocyano, —SR, —SOR. —$SO_2$R, —$NHSO_2$R, —$(C_1$–$C_6)$alkoxy, —$NR^1R^2$, —$NHCOR^1$, —$CONR^1R^2$, Ph, —COR, COOR, —$(C_1$–$C_6)$alkyl, —$(C_1$–$C_6)$alkyl substituted with one to six halogens, —$(C_3$–$C_6)$cycloalkyl and trifluoromethoxy;
each and every R, $R^1$, and $R^2$ is independently selected from the group consisting of hydrogen, —$(C_1$–$C_6)$ alkyl, —$(C_1$–$C_6)$alkyl substituted with one to thirteen halogens selected from the group consisting of fluorine, chlorine, bromine, and iodine, phenyl, benzyl, —$(C_2$–$C_6)$alkenyl, —$(C_3$–$C_6)$cycloalkyl and $(C_1$–$C_6)$ alkoxy; and
each and every $R^3$ and $R^4$ is independently selected from a group consisting of hydrogen, methyl, ethyl, n-propyl and i-propyl, wherein the serotonin reuptake inhibitor is sertraline, fluoxetine, fenfluran,ine, or fluvoxainine.

2. The pharmaceutical composition according to claim 1 wherein Ar is phenyl, naphthyl, benzoxazolonyl, indolyl, indolonyl, benzirnidazolyl, or quinolyl;
$Ar^1$ is phenyl, pyridmyl, pyridazinyl, pyrimidinyl, or pyrazinyl;
A is O, S, $SO_2$, CHOH or $CH_2$;
n is 0 or 1; and
wherein Ar and $Ar^1$ are independently and optionally substituted with up to three substiuents independently selected from the group consisting of fluoro, chioro, nitro, cyano, —$NR^1R^2$, —$(C_1$–$C_6)$alkoxy, COOR, —$CONR_1R_2$, and —$(C_1$–$C_6)$alkyl.

3. The pharmaceutical composition according to claim 2 wherein A is O,S or $CH_2$.

4. The pharmaceutical composition according to claim 2 wherein Ar is optionally substituted phenyl; $Ar^1$ is optionally substituted and is selected from the group consisting of phenyl, pyridinyl, and pyrimidinyl; A is 0 and n is 1.

5. The pharmaceutical composition according to claim 4 wherein A is 0, n is 1, $Ar^1$ is 5-fluoropyrimidin-2-yl and Ar is optionally substituted phenyl, provided it is not p-fluorophenyl.

6. The pharmaceutical composition according to claim 1 wherein A is O or S. n is 1 and Ar is phenyl or substituted phenyl.

7. The pharmaceutical composition according to claim 4 wherein $Ar^1$ is 5-fluoropyrimidin-2-yl or pyrimidin-2-yl.

8. The pharmaceutical composition according to claim 7 wherein $Ar^1$ is 5-fiuoro-pyrimidin-2-yl.

9. The pharmaceutical composition according to claim 1 wherein the compound of Formula I is
  (7S,9aS)-7-((3-Methyl-phenoxy)methyl-2-(5-fluoropyrimidin-2-yl)-2,3,4,6,7,8,9,9a-octahydro-1H-pyrido[1,2-a]pyrazine;
  (7S,9aS)-7-(3-carbomethoxy-phenoxy)methyl-2-(5-fluoropyrimidin2-yl)-2,3,4,6,7,8,9,9a-octahydro-1H-pyrido[1,2-a]pyrazine;
  (7S,9aS)-7-(3-nitro-phenoxy)methyl-2-(5-fluoropyrimidin-2-yl)-2,3,4,6,7,8,9,9a-octahydro-1-H-pyrido[1,2-a]pyrazine;
  (7S,9aS)-7-(3-cyano-phenoxy)methyl-2-(5-fluoropyrimidin-2-yl)-2,3,4,6,7,8,9,9a-octahydro-1H-pyrido[1,2-a]pyrazine;
  (7S,9aS)-7-(3-methoxy-phenoxy)methyl-2-(5-fluoropyrimidin-2-yl)-2,3,4,6,7,8,9,9a-octahydro-1H-pyrido[1,2-a]pyrazine;
  (7S,9aS)-7-(3-acetamido-phenoxy)methyl-2-(5-fluoropyrimidin-2-yl)-2,3,4,6,7,8,9,9a-octahydro-1H-pyrido[1,2-a]pyrazine; or
  (7S,9aS)-7-(3-(1,1-dimethyl)ethyl-phenoxy)methyl-2-(5-fluoropyrimidin-2-yl)-2,3,4,6,7,8,9,9a-octahydro-1H-pyrido[1,2-a]pyrazine;
and pharmaceutically acceptable salt thereof.

10. A pharmaceutical composition comprising an effective amount of a compound of the formula I

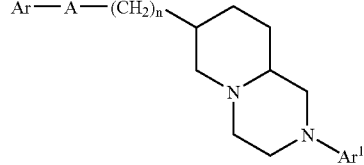

or pharmaceutically acceptable salts thereof in combination with a serotonin-2 receptor, antagonist, wherein
Ar is phenyl, naphthyl, benzoxazolonyl, indolyl. indolonyl, benzimida.zoly, quinolyl, furyl, benzofuryl. thienyi, benzothienyl, oxazolyl, or benzoxazolyl;
$Ar^1$ is phenyl, pyridinyl, pyridazinyl, pynmidinyl, or pyrazinyl;
A is O, S, $SO_2$, C=O, CHOH or $(CR^3R^4)$—;
n is 0, 1 or 2;
each of Ar and $Ar^1$ may be independently and optionally substituted with one to four substituents independently from the group consisting of fluoro, chioro, bromo, jodo, cyano, nitro, thiocyano, —SR. —SOR, —$SO_2$R, —$NHSO_2$R, —$(C_1$–$C_6)$alkoxy, —$NR^1R^2$, —$NHCOR^1$, —$CONR^1R^2$, Ph, —COR, COOR, —$(C_1$–$C_6)$ alkyl, —$(C_1$–$C_6)$allcyl substituted with one to six halogens, —$(C_3$–$C_6)$cycloalkyl and trifluoroinethoxy;
each and every R, $R^1$, and $R^2$ is independently selected from the group consisting of hydrogen, —$(C_1$–$C_6)$ alkyl, —$(C_1$–$C_6)$alkyl substituted with one to thirteen halogens selected from the group consisting of fluorine, chlorine, bromine, and iodine, phenyl, benzyl. —$(C_2$–$C_6)$alkenyl, —$(C_3$–$C_6)$cycloalkyl and —$(C_1$–$C_6)$alkoxy; and each and every R³ and R⁴ is independently selected from a group consisting of hydrogen, methyl, ethyl, n-propyl and i-propyl, wherein the serotonin-2 receptor antagonist is of the formula $$F-\text{Ph}-R_a-(CH_2)_{qa}-T \quad \text{wherein}$$

$R_a$ is

[structures shown]

T is

[structures shown]

D is H, C₁-C₄alkyl or phenyl; and qa is 1, 2, 3 or 4.

11. The pharmaceutical composition according to claim 10 wherein Ar is phenyl, naphthyl, benzoxazolonyl, indolyl, indolonyl, benzimidazoly, or quinolyl;

Ar¹ is phenyl, pyridinyl, pyndazinyl, pyrimidinyl, or pyrazinyl;

A is O, S. SO₂, CHOH or CH₂;

n is 0 or 1; and wherein Ar and Ar¹ are independently and optianally substituted with up to three substituents independently selected from the group consisting of fluoro, chioro, nitro, cyano, —NR¹R², —(C₁–C₆)alkoxy, COOR, —CONR₁R₂, and —(C₁–C₆)alkyl.

12. The pharmaceutical composition according to claim 11 wherein A is O, S or CH₂.

13. The pharmaceutical composition according to claim 11 wherein Ar is optionally substituted phenyl; Ar¹ is optionally substituted and is selected from the group consisting of phenyl, pyridinyl, and pyrimidinyl; A is O and n is 1.

14. The pharmaceutical composition according to claim 13 wherein A is 0, n is 1, Ar¹ is 5-fluoropyrimidin-2-yl and Ar is optionally substituted phenyl, provided it is not p-fluorophenyl.

15. The pharmaceutical composition according to claim 10 wherein A is O or S, n is 1 and Ar is phenyl or substituted phenyl.

16. The pharmaceutical composition according to claim 13 wherein Ar¹ is 5-fluoropyrimidin-2-yl or pyrixnidin-2-yl.

17. The pharmaceutical composition according to claim 13 wherein Ar¹ is 5-fluoro-pyrimidin-2-yl.

18. The pharmaceutical composition according to claim 10 wherein the compound of Formula I is (7S,9aS)-7-((3-MeEhy1-phenoxy)methyl-2-(5-fluoropyrdin-2,3,4,6,7,8,9,9a-octahydro-1H-pyrido[1,2-a]pyrazine;

(7S,9aS)-7-(3-carbomethoxy-phenoxy)methyl-2-(5-fluoropyrimidin-2-yl)-2,3,4,6,7,8,9,9a-octahydro-1H-pyrido[1,2-a]pyrazine;

(7S,9aS)-7-(3-nitro-phenoxy)methyl-2-(5-fluoropyrimidin-2-yl)-2,3,4,6,7,8,9,9a-octahydro-1H-pyrido[1,2-a]pyrazine;

(7S,9aS)-7-(3-cyano-phenoxy)methyl-2-(5-fluoropyrimidin-2-yl)-2,3,4,6,7,8,9,9a-octahydro-1H-pyrido[1,2-a]pyrazine;

(7S,9aS)-7-(3-methoxy-phenoxy)methyl-2-(5-fluoropyrimidin-2-yl)-2,3,4,6,7,8,9,9a-octahydro-1H-pyrido[1,2-a]pyrazine;

(7S,9aS)-7-(3-acetamido-phenoxy)methyl-2-(5-fluoropyrimidin-2yl)-2,3,4,6,7,8,9,9a-octahydro-1H-pyrido[1,2-a]pyrazine;

(7S,9aS)-7-(3-(1,1-dimethyl)ethyl-phenoxy)methyl-2-(5-fluoropyrimidin-2-yl)-2,3,4,6,7,8,9,9a-octahydro-1H-pyrido[1,2-a]pyrazine;

and pharmaceutically acceptable salt thereof.

19. A pharmaceutical composition comprising an effective amount of a compound of the formula I $$Ar-A-(CH_2)_n-\text{[structure]}-Ar^1 \qquad I$$

or pharmaceutically acceptable salts thereof in combination with a serotonin-2 receptor, antagonist, wherein Ar is phenyl, naphthyl, benzoxazolonyl, indolyl, indolonyl, benzimidazolyl, quinolyl, furyl, bcnzofuryl, thienyl, benzothienyl. oxazolyl, or benzoxazolyl;

Ar¹ is phenyl, pyridinyl, pyridazinyl, pyrirnidinyl, or pyrazinyl;

A is O, S, SO₂, C=O, CHON or (CR³R⁴)—;

n is 0, 1 or 2;

each of Ar and Ar¹ may be independently and optionally substituted with one to four substituents independently from the group consisting of fluoro, chioro, bromo, jodo, cyano, nitro, thiocyano, —SR, —SOR, —SO₂R, —NHSO₂R, —(C₁–C₆)alkoxy, —NR¹R², —NHCOR¹, —CONR¹R², Ph, —COR, COOR, —(C₁–C₆)alkyl, —(C₁–C₆)alkyl substituted with one to six halogens, —(C₃–C₆)cycloalkyl and trifluoromethoxy;

each and every R, $R^1$, and $R^2$ is independently selected from the group consisting of hydrogen, —($C_1$–$C_6$)alkyl, —($C_1$–$C_6$)alkyl substituted with one to thirteen halogens selected from the group consisting of fluorine, chlorine, bromine, and iodine, phenyl, benzyl, —($C_2$–$C_6$)alkenyl, —($C_3$–$C_6$)cycloalkyl and ($C_1$–$C_6$)alkoxy; and each and every $R^3$ and $R^4$ is independently selected from a group consisting of hydrogen, methyl, ethyl, n-propyl and i-propyl wherein the serotonin-2 receptor antagonist is ketanserin, pelanserin, pipamperone, spiperone, pireneperin, or ritanserin.

* * * * *